(12) United States Patent
Lamango et al.

(10) Patent No.: US 6,372,793 B1
(45) Date of Patent: Apr. 16, 2002

(54) METHOD FOR TREATMENT OF A NEUROLOGICAL DISEASE CHARACTERIZED BY IMPAIRED NEUROMODULATOR FUNCTION

(75) Inventors: Nazarius S. Lamango; Clivel G. Charlton, both of Tallahassee, FL (US)

(73) Assignee: Florida Agricultural & Mechanical University, Tallahassee, FL (US)

(*) Notice: Subject to any disclaimer, the term of this patent is extended or adjusted under 35 U.S.C. 154(b) by 0 days.

(21) Appl. No.: 09/642,576

(22) Filed: Aug. 19, 2000

Related U.S. Application Data
(60) Provisional application No. 60/150,000, filed on Aug. 20, 1999.

(51) Int. Cl.[7] ...................... A61K 31/195; A61K 31/20; A61K 31/19
(52) U.S. Cl. ...................... 514/562; 514/560; 514/557; 514/568
(58) Field of Search ................................. 514/562, 560, 514/557, 568

(56) References Cited

U.S. PATENT DOCUMENTS

| | | |
|---|---|---|
| 5,202,456 A | 4/1993 | Rando |
| 5,571,687 A | 11/1996 | Casey et al. |
| 5,705,528 A | 1/1998 | Kloog |
| 5,789,439 A | 8/1998 | Hosono et al. |

OTHER PUBLICATIONS

Nazarius S. Lamango and Clivel G. Charlton, Farnesyl–L–Cysteine Analogs Block SAM–Induced Parkinson's Disease–Like Symptoms in Rats. *Pharmacology Biochemistry and Behavior*, vol. __. No. __, pp. 1–9, 2000.

Nazarius S. Lamango, Robert A. Nesby and Clivel G. Charlton, Quantification of S–Adenosylmethionine–Induced Tremors: A Possible Tremor Model for Parkinson's Disease. *Pharmacology Biochemistry and Behavior*. vol. 65, No. 3, pp. 523–529, 2000.

M.S. Yassin, H. Cheng, J. Ekblom and L. Oreland, Inhibitors of catecholamine metabolizing enzymes cause changes in S–adenosylmethionine and S–adenosylhomocysteine in the rat brain. *Neurochem .Int.* 32 (1998) 53–59.

H. Cheng, C. Gomes–Trolin, S.–M. Aquilonius, A. Steinberg, C. Löfberg, J. Ekblom, and L. Oreland, Levels of L–Methionine S–Adenosyltranferase Activity in Erythrocytes and Concentrations of S–Adenosylmethionine and S–Adenosylhomocysteine in Whole Blood of Patients with Parkinson's Disease. *Experimental Neurology* 145, 580–585 (1997) Article No. EN976466.

Teodoro Bottiglieri, Keith Hyland and Edward H. Reynolds, The Clinical Potential of Ademetionine (S–Adenosylmethionine) in Neurological Disorders. *Drugs* 48(2), pp. 137–152, 1994.

Lesley D. Morrison, David D. Smith, and Stephen J. Kish, Brain S–Adenosylmethionine Levels Are Severely Decreased in Alzheimer's Disease. *Journal of Neurochem*, vol. 67, No. 3, 1996.

Michael A. Collins, Edward J. Neafsey, Kazuo Matsubara, Robert J. Cobuzzi Jr. and Hans Rollema, Indole–N–methylated B–carbolinium ions as potential brain–bioactivated neurotoxins. *Brain Research*, 570 (1992) pp. 154–160.

Debra A. Gearhart, Edward J. Neafsey and Michael A. Collins, Characterization of Brain B–Carboline–2–N–Methyltransferase, An Enzyme That May Play a Role in Idiopathic Parkinson's Disease. *Neurochemical Research*, vol. 22, No. 2, 1997, pp. 113–121.

Kazuo Matsubara, Edward J. Neafsey and Michael A. Collins, Novel S–Adenosylmethionine–Dependent indole–NMethylation of B–Carbolines in Brain Particulate Fractions. *Journal of Neurochemistry*, vol. 59, No. 2, 1992. pp. 511–518.

Toshiharu Nagatsu, Isoquinoline neurotoxins in the brain and Parkinson's disease. *Neuroscience Research* 29 (1997) 99–111.

Kazuo Matsubara, Michael A. Collins, Atsushi Akane, Jun Ikebuchi, Edward J. Neafsey, Masato Kagawa and Hiroshi Shiono, Potential bioactivated neurotoxicants, N–methylated B–carbolinium ions, are present in human brain. *Brain Research*, 610 (1993) 90–96.

Martti Törnwall and Pekka T. Männistö, Effects of three types of catechol O–methylation inhibitors on L–3, 4–dihydroxyphenylalanine–induced circling behavior in rats. *European Journal of Pharmacology*, 250 (1993) 77–84.

Clivel G. Charlton and Bernard Crowell, Jr., Effects of Dopamine Metabolites On Locomotor Activities And On The Binding Of Dopamine: Relevance To The Side Effects Of L–Dopa. *Life Sciences*, vol. 66, No. 22, pp. 2159–2171, 2000.

(List continued on next page.)

*Primary Examiner*—William R. A. Jarvis
(74) *Attorney, Agent, or Firm*—Allen, Dyer, Doppelt, Milbrath & Gilchrist, P.A.

(57) ABSTRACT

A method for treatment of a mammalian neurological disease characterized by impaired neuromodulator function, the method comprises administering a therapeutically effective amount of a composition including a compound of a prenylcysteine or an analog thereof in a pharmaceutically acceptable carrier. The compound comprises a prenylcysteine or analog thereof selected from farnesylcysteine, N-acetylfarnesylcysteine, N-acetylgeranylcysteine, N-acetylfanesylcysteine, N-acetylgeranylcysteine, farnesyl-2-mercaptoethanesulfonic acid, farnesylthioacetic acid, and farnesylmercaptosuccinic acid.

18 Claims, 21 Drawing Sheets

OTHER PUBLICATIONS

X.X. Liu, K. Wilson and C.G. Charlton, Effects Of L–Dopa Treatment On Methylation In Mouse Brain: Implications For The Side Effects Of L–Dopa. *Life Sciences*, vol. 66, No. 23, pp. 2277–2288, 2000.

K. A. Baker, M. Hong, D. Sadi, and I. Mendez, Intrastriatal and Intranigral Grafting Of hNT Neurons in the 6–OHDA Rat Model of Parkinson's Disease, *Experimental Neurology*, 162, 350–360 (2000).

Y.He, T. Lee, S.K. Leong, 6–Hydroxydopamine induced apoptosis of dopaminergic cells in the rat substantia nigra, *Brain Research* 858 (2000) 163–166.

A. Woodgate, G. Macgibbon, M. Walton, M. Dragunow, The toxicity of 6–hydroxydopamine on PC12 and P19 Cells, *Molecular Brain Research*, 69 (1999) 84–92.

I. Mendez, K.A. Baker, M. Hong, Simultaneous intrastriatal and intranigral grafting (double grafts) in the rat model of Parkinson's disease, *Brain Research Reviews*, 32 (2000) 328–339.

Anthone W. Dunah, et al. Alterations in Subunit Expression, Composition, and Phosphorylation of Striatal N–Methyl-D–Aspertate Glutamate Receptors in a Rat 6–Hydroxydopamine Model of Parkinson's Disease, *Molecular Pharmacology*, 57 342–352. (2000).

D. I. Finkelstein, et al. Axonal Sprouting Following Lesions Of The Rat *Substantia Nigra, Neuroscience*, vol. 97 No. 1. pp. 99–112 (2000).

Chong S. Lee, M. Angela Cenci, Michael Schulzer and Adners Björklund. Embryonic ventral mesencephalic grafts improve levodopa–induced dyskinesia in a rat model of Parkinson's disease, *Brain* (2000), 123, 1365–1379.

Naoyuki Nakao, M.D., Hideyuki Yokote, M.D., Kunio Nakai, M.D., and Toru Itakura, M.D. Promotion of survival and regeneration of nigral dopamine neurons in a rat model of Parkinson's disease after implantation of embryonal carcinoma–derived neurons genetically engineered to produce glial cell line–derived neurotrophic factor, *J. Neurosurg*, /vol. 92/ Apr., 2000. pp. 659–670.

Sandra Green, Steve Buttrum, Helen Molloy, et al. N–methylation of Pyridines in Parkinson's disease, *The Lancet*, vol. 338: Jul. 13, 1991, pp. 120–121.

R. H. Waring, S. G. Sturman, et al. S–Methylation In Motorneuron Disease And Parkinson's Disease, *The Lancet*, Aug. 12, 1989, pp. 356–357.

AFC

FTP

FTS

METHOD FOR TREATMENT OF A NEUROLOGICAL DISEASE CHARACTERIZED BY IMPAIRED NEUROMODULATOR FUNCTION

RELATED APPLICATION

This application claims priority from provisional patent application Ser. No. 60/150,000, which was filed on Aug. 20, 1999.

FIELD OF THE INVENTION

The present invention relates to the field of neurological dysfunction and, more particularly to a neurological disease characterized by impairment of neuromodulator function, as in Parkinson's disease.

BACKGROUND OF THE INVENTION

Parkinson's disease (PD) is characterized by tremors, hypokinesia, rigidity and abnormal posture as the principal visible symptoms. The tremors in PD are of the resting type, since they occur when the muscles are in a state of relaxation. Its main pathological feature is the degeneration of dopaminergic neurons which have their cell bodies in the substantia nigra and their terminals projecting into the neostriatum. Dopamine is thus significantly depleted in the neostriatum of PD patients. Changes to the substantia nigra and the neostriatal complex are linked to the tremors seen in PD. Compounds that damage the nigrostriatal dopaminergic system and cause hypokinesia, rigidity and tremors have the potential to be used as models for studying PD. Chemical agents such as 1-methyl-4-phenyl-1,2,3,6-tetrahydropyridine (MPTP) and 6-hydroxydopamine (6-OHDA) damage the nigrostriatal dopaminergic neurons and are widely used to induce symptoms of PD. The effectiveness of these compounds rely on their ability to cause significant damage to the nigrostriatal dopaminergic system. The levels of symptoms are apparently dependent on the degree of nigrostriatal damage, which is somewhat difficult to control. As a result, the symptoms produced by these agents are predominantly rigidity, hypokinesia and poverty of movements and are not always consistent. Tremor, the most conspicuous symptom of PD is not a characteristic feature of the MPTP and 6-OHDA models.

Despite the abundant knowledge regarding the behavioral and pathological features of PD, the actual cause of Parkinson's disease symptoms and neurodegeneration remains elusive. Although dopamine depletion has been shown to be a common feature, it is unclear whether this is due mainly to the loss of the dopamine producing cells themselves. PD models such as that of MPTP, a synthetic compound, do not explain cases of familial Parkinsonism. The present model, however, is based on S-adenosylmethionine (SAM), an endogenous compound that is widely distributed within body tissues. This implies that environmental and genetic factors that induce aberrant changes in its synthesis and use may result in disease conditions. It has been reported that injecting SAM into the lateral ventricles of rodents caused the principal symptoms observed in PD (Charlton, 1990, Charlton and Crowell, Jr., 1995, Charlton and Way, 1978, Crowell, Jr. et al, 1993). Most importantly, tremors were routine and always in association with hypokinesia, rigidity and abnormal posture. SAM injections also caused dopaminergic system degeneration as depicted by the loss of tyrosine hydroxylase immunoreactivity in the nigrostriatum and forebrain (Charlton, 1997).

Without a known cause, no cure or preventive measures have been derived for PD. Clinical management of PD has often involved the use of L-DOPA (Pfeiffer, 1998), an intermediate in the dopamine biosynthetic pathway. The general consensus is that L-DOPA, which is more accessible to the central nervous system than dopamine, is taken up by dopaminergic neurons and enzymatically converted to the active neurotransmitter, thus replenishing the depleted dopamine. It has been proposed that SAM-dependent methylation of dopamine by catechol-o-methyltransferase (COMT) may also deplete DA. COMT inhibitors are therefore being explored as PD medications (Pfeiffer, 1998).

SAM-dependent methylation of molecules capable of altering dopaminergic transmission is by no means limited to DA and its metabolites. Nucleic acid methylation is believed to influence gene expression (Chiang et al. 1996). Deleterious changes in gene regulation may precipitate neurodegeneration similar to that encountered in PD. Also, since many studies have concentrated on events leading to the synthesis and release of dopamine, defects in such important phenomena as the transmission of signals from the post synaptic receptors following dopamine receptor binding are yet to be explored for possible links to PD.

Following release, dopamine initiates a chain of events by binding to the post synaptic dopamine receptor. The dopamine receptors belong to a class of membrane-spanning receptors that interact with the GTP-binding proteins known as heterotrimeric G-proteins (Gudermann et al, 1996). Multiple forms of the respective monomers exist with varying degrees of amino acid sequence similarity. Of the three subunits, the γ-subunit undergoes the post-translational modification with either a C15 (trans,trans-farnesyl) or a C20 (all trans-geranylgeranyl)isoprenyl unit. A consensus amino acid sequence (CaaX, where C is cysteine, a is any aliphatic amino acid and X is the carboxyl terminal amino acid) directs the S-prenylation of a cysteine residue (Sinensky and Lutz, 1992). The terminal tripeptide is proteolytically removed (Hrycyna and Clarke, 1992) thus exposing a C-terminally prenylated protein that is capable of undergoing reversible SAM-dependent methylation (Perez-Sala et al, 1991). The γ-subunits, which vary in size from 5 to 7.5 kDa (Cali et al, 1992), exist in a stable heterodimer complex with the β-subunit, the βγ-complex only transiently interacting with the α-subunit (Clapham and Neer, 1997). The α-subunit and the βγ-complex interact with various cellular effector enzymes and ion channels (Clapham and Neer, 1997). For example, the βγ-complex was found to inhibit the activity of $Ca^{2+}$/calmodulin-stimulated type-I adenylylcyclase but increased that of stimulatory recombinant Γα-stimulated type-II adenylyl cyclase (Iniguez-Lluhi et al., 1992). These effects on the enzyme activities were found to be dependent on the C-terminal isoprenylation (Iniguez-Lluhi et al., 1992). The βγ-complex also binds to and influences the activity of voltage-dependent calcium channels (De Waard et al., 1997) and binds to immobilized Raf-1 protein kinase with a nanomolar dissociation constant (Pumiglia et al, 1995). It is not clear what role methylation may play in these processes, if any.

Farnesylcysteine (FC) and geranylgeranylcysteine (GGC) analogs that mimic the C-terminal portion of the prenylated G-protein γ-subunit influence a variety of cellular processes. For example, farnesylthiosalicylate (FTS) increased intracellular calcium concentrations of differentiated HL60 cells and stimulated superoxide release by HL60 cells and polymorphonuclear leukocytes (Tisch et al., 1996). In neutrophils, FC analogs either initiated or inhibited superoxide-release (Ding et al., 1994). FC analogs inhibited [$^{35}$S]GTP[S] binding to washed membranes of myeloid-differentiated HL60 cells (Scheer and Gierschik, 1993, 1995) and capacitative calcium entry into cells (Xu et al., 1996). Although these compounds are avid methyl acceptors and/or competitively inhibit the SAM-dependent methylation of prenylated proteins (Perez-Sala et al., 1992), the cellular phenomena outlined above are believed to be independent of methylation (Scheer and Gierschik, 1993, 1995, Ding et al., 1994).

The possibility has not been investigated that other molecules involved with dopamine signaling such as the G-protein γ-subunit may indeed be hypermethylated and could account for the observed PD symptoms. Methylation has been exert a strong influence on some physiological phenomena. For example, a strong dependence on methylation for the activation of phosphatidylinositol-specific phospholipase C has been reported (Parish et al., 1995). Methylation inhibitors were found to modulate nutrient-induced insulin secretion from rat islets (Metz et al, 1993), permeabilized HIT-T15 cells (Regazzi et al., 1995) and amylase secretion by pancreatic acini (Capdevila et al., 1997). Strains of *Schizosaccharomyces pombe* with a defective mam4 gene that encodes the prenylated protein methyl transferase produce non-methylated, inactive M-factor (Imai et al., 1997). Additionally, demethylation of *S. cerevisiae* a-factor resulted in loss of biological activity (Anderegg et al, 1988).

SUMMARY OF THE INVENTION

With the foregoing in mind, the present invention advantageously provides a method of substantially reversing a methylation imbalance and its effects in mammalian neural tissue thereby aiding in restoring neuromodulator function. The method comprises contacting the neural tissue with an effective amount of a prenylcysteine compound or a pharmaceutically acceptable analog thereof. The invention also provides a method for treatment of a mammalian neurological disease characterized by impaired neuromodulator function. The treatment method comprises administering a therapeutically effective amount of a composition including a prenylcysteine compound or an analog thereof in a pharmaceutically acceptable carrier. Also included in the invention is a composition for treating a mammalian neurological disease characterized by impaired neuromodulator function. The composition comprises a therapeutically effective amount of a prenylcysteine compound or a pharmaceutically acceptable analog thereof.

Parkinson's disease (PD)-like tremors, hypokinesia, rigidity and postural abnormalities were dose-dependently induced in rats by intracerebroventricular (icv) injections of S-adenosylmethionine (SAM). A method for quantifying the tremors was devised. The symptoms appeared within 0.5–2 min, peaked within 10 min while recovery occurred about 90 min after SAM injection. The PD-like symptoms were not significantly affected by the inhibitor of SAM-dependent methylation, S-adenosylhomocysteine (SAH), L-DOPA and N-acetyldopamine. [$^3$H-methyl]SAM reacted with rat nerve cell membranes in a timely, specific and irreversible manner. Icv injection of [$^3$H-methyl]SAM resulted in the methylation of a 5 kDa molecule within the same time as the PD-like symptoms, whose chromatographic mobility on a gel-filtration column was altered by denaturation with 6 M guanidine hydrochloride, suggesting possible association with another molecule. Lyophilized aliquots of the radioactive peak fractions released a volatile radioactive compound on incubation with 1 M sodium hydroxide solution. Since PD involves the loss of dopaminergic function, and dopamine signaling is mediated by receptors that interact with trimeric G-proteins whose γ-subunits exist in dimeric complexes with the various β-subunits, range in size between 5 and 7 kDa, are prenylated and undergo reversible C-terminal carboxylmethylation, farnesylcysteine (FC) analogs were synthesized and tested to further understand the mechanism by which SAM-induces the PD-like symptoms. The FC analogs, which are modeled on the isoprenylated C-terminal of the G-protein γ-subunit, blocked the tremors, rigidity, abnormal posture and not only reversed the hypokinesia but also caused a significant degree of hyperactivity in the experimental animals. This indicates the specificity of the compounds for alleviating the symptoms, and suggests the need for titrating the compounds to determine an effective therapeutic dose. The FC analogs potentiated the amphetamine-induced rotation of 6-hydroxydomaine-lesioned rats. This effect harmonizes our model with at least one other PD model. It also indicates by increasing the effect of dopamine released by the amphetamine injection that 1) SAM induces PD symptoms by affecting the DA signaling pathway, 2) the SAM effect could be corrected by injecting the animals with FC analogs, and 3) giving an amount that surpassed a dose sufficient to obviate the SAM-induced effects could cause a significant degree of hyperactivity. Since SAM and the prenylated proteins naturally coexist in the brain, it is possible that PD symptoms can be precipitated in some individuals through an aberration in the methylation/demethylation homeostasis. Such an imbalance may occur as a result of environmental and/or genetic factors that take effect gradually with aging. The results of our study indicate that derivatives of isoprenyl compounds (geranyl-, farnesyl- and geranylgeranyl-) substantially reverse the deleterious effects of the methylation/demethylation imbalance in neural tissue.

In the studies developing the present invention, we have reported that SAM induced PD-like symptoms in rats are associated with the in vivo methylation of molecules of about 5 kDa in size, which is around the molecular weight range of the trimeric G-protein γ-subunit. Lyophilized aliquots of the chromatographic peak fractions containing the methylated products from brain extracts released volatile radioactive groups on incubation with NaOH, suggesting the possible involvement of carboxylic acid moieties. Furthermore, the SAM-induced PD symptoms were blocked if the SAM injections were preceded by an effective dose of an FC analog. The FC analogs not only blocked the tremors and reversed the hypokinesia, rigidity and postural abnormalities but also caused most of the injected animals to engage in persistent hyperactivity. Furthermore, the FC analogs significantly increased amphetamine-induced rotation of 6-OHDA-lesioned rats, thus suggesting that these compounds could be acting directly on the DA signaling pathway. This effect on the 6-OHDA-lesioned rats also underscores the link between the present SAM-PD animal model and previous PD models.

The method of the invention substantially reverses a methylation/demethylation imbalance in mammalian neural tissue to thereby restore neuromodulator function. The neuromodulator also comprises a neurotransmitter receptor site and, particularly, a receptor site for dopamine. The method is accomplished by contacting the neural tissue with an effective amount of a compound including prenylcysteine or a pharmaceutically acceptable analog thereof. The compound in the method is preferably selected from farnesylcysteine, N-acetylgeranylcysteine, N-acetylfanesylcysteine, N-acetylgeranylgeranylcysteine, farnesyl-2-mercaptoethanesulfonic acid, farnesylthioacetic acid, farnesylmercaptosuccinic acid, farnesylthiolactic acid, and farnesylthiotriazole.

The invention also includes a composition and a method for treatment of a mammalian neurological disease characterized by impaired neuromodulator function, preferably wherein the impairment is characterized by a methylation/demethylation imbalance. The method comprises administering a therapeutically effective amount of a composition including a prenylcysteine compound or an analog thereof in a pharmaceutically acceptable carrier.

BRIEF DESCRIPTION OF THE DRAWINGS

Some of the features, advantages, and benefits of the present invention having been stated, others will become apparent as the description proceeds when taken in conjunction with the accompanying drawings, which are described below.

DETAILED DESCRIPTION OF THE PREFERRED EMBODIMENT

Figure 1:
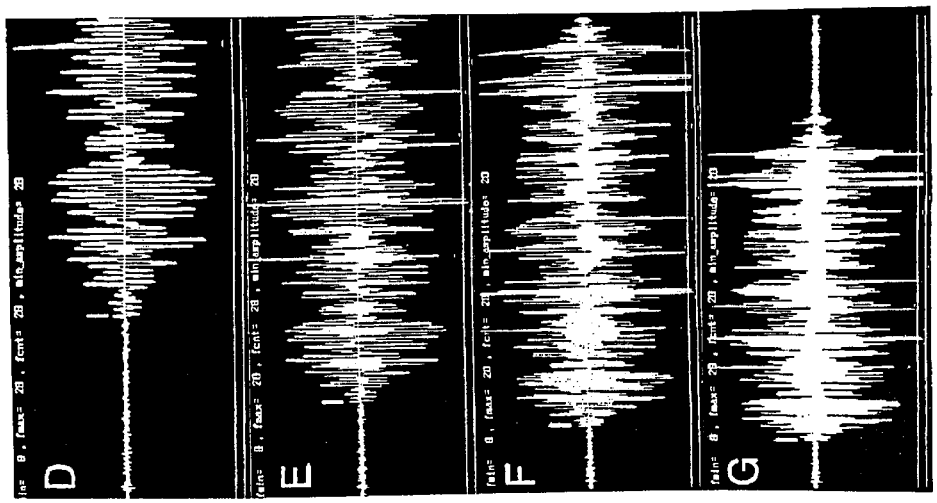
FIGS. 1(A–G): Segments of Tremor Monitor activity profiles. Rats were cannulated as described in the methods section. At least two days after cannulation, they were Icv injected with either PBS or 1 mmmol of SAM and their movements recorded using the Tremor Monitor. Recorded sections from animals injected either with PBS (panel A) or 1 mmmol SAM (panels B and C). In each case, the time axis of the activity profile has been condensed 41-fold. Recorded section from an animal injected with 1 mmmol of SAM after the time axis of the activity profile was condensed 11— (panel D), 21—(panel E), 31—(panel F) and 41-fold, respectively.
Figure 1:
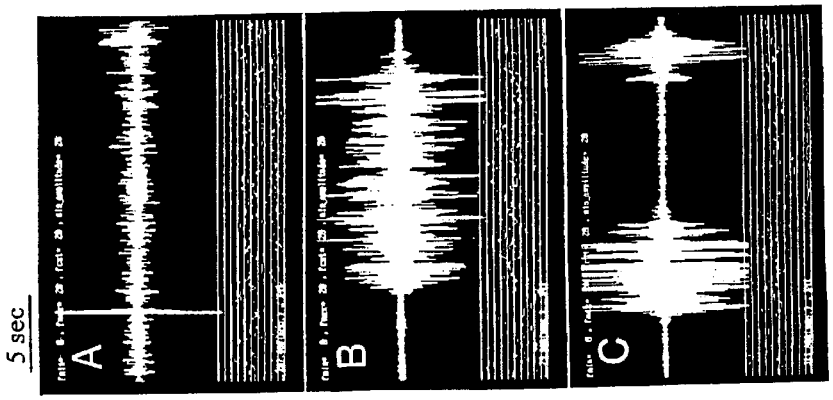

The present invention will now be described more fully hereinafter with reference to the accompanying drawings, in which preferred embodiments of the invention are shown. This invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art.

The experimental techniques employed in the development of the present invention are set forth in detail below, including experimental examples. In addition, as used herein, the term "prenylcysteine" is intended to include all those analogs synthesized with the geranyl—(10 carbon atoms) and geranylgeranyl—(20 carbon atoms) in addition to farnesyl-analogs (15 carbon atoms). The term "neuromodulator" indicates a component involved in regulation of neural signals, and includes a neurotransmitter receptor site, such as for dopamine.

Materials and Methods

Materials

Male Sprague-Dawley rats weighing 200–300 g obtained from Harlam Laboratories, Ohio, were maintained under laboratory conditions of about 12 h light and 12 h dark cycle with water and food supply ad libitum, as described before (Charlton and Mack, 1994). S-Adenosyl-L-methionine (SAM, chloride salt), L-dihydroxyphenylalanine (L-DOPA), N-acetyldopamine (NADA), S-adenosyl-L-homocysteine (SAH), N-acetyl-L-cysteine, 3-mercaptopropionic acid, thiosalicylic acid, trans,trans-farnesyl bromide, Sephacryl S-100-HR (Pharmacia Biotech, Upssala, Sweden), gel-filtration molecular weight standards, d-amphetamine sulfate and 6-hydoxydopamine were purchased from Sigma Chemical Co., St. Louis, Miss. S-[methyl-$^3$H]-SAM was supplied by DuPont NEN Research Products, Boston, Mass. The tremor recording apparatus (Tremor-Scan Monitor, Accuscan Electronics, Inc., Columbus, Ohio) consisted of a sensor assembly which generates waves with amplitudes and frequencies determined by the forces and the rate of the movements generating the forces, the interface unit with gain and baseline adjustments and an IBM compatible personal computer. This apparatus records and stores the activity profile from the sensor assembly in a continuous, time-dependent manner for subsequent analysis.

N-acetyl-S-farnesyl-L-cysteine (AFC), S-farnesylthiopropionic acid (FTP) and farnesylthiosalicylic acid (FTS) were synthesized as described by Tan et al. (1991). These were purified on silica gel and shown by TLC to be over 95% pure. The structures were confirmed by NMR spectroscopy.

Synthesis of FC Analogs: Geranylgeraniol, geranyl chloride, trans, trans-farnesyl bromide, thiolactic acid, mercaptosuccinic acid, thioacetic acid, 2-mercaptoethanesulfonic acid and 1H-1,2,4-triazole-3-thiol were purchased from Sigma-Aldrich. All trans-geranylgeranyl bromide was synthesized from all trans-geranylgeraniol and phosphorus tribromide according to the method of Fukuda et al. (1981). The resulting all trans-geranylgeranyl bromide was reacted with N-acetylcysteine to form N-acetyl all trans-geranylgeranylcysteine (AGGC) according to the method of Tan et al. (1991). N-acetylgeranylcysteine (AGC) was synthesized from geranyl bromide and N-acetyl cysteine as previously described (Tan et al., 1991). Farnesyl-2-mercaptoethanesulfonic acid (FTE), farnysylthioacetic acid (FTA), farnesylmercaptosuccinic acid (FMS), farnesylthiolactic acid (FTL) and farnesylthiotriazole (FTT) were each synthesized from trans, trans-farnesyl bromide and 2-mercaptoethanesulfonic acid, thioacetic acid, mercaptosuccinic acid, thiolactic acid and 1,2,4-triazole-3-thiol, respectively, according to the procedure of Tan et al. for the synthesis of FC analogs (1991).

Phosphate buffered saline (PBS) was prepared according to the following formula: $Na_2HPO_4$ (1.9 mM), $NaH_2PO_4$ (4.29 mM), NaCl (138 mM), KCl (2.7 mM).

Representative formulas for these compounds are shown in Table 1, on the following page.

Monitoring of SAM-Induced Tremors

Rats were cannulated for subsequent injections into the lateral ventricle as previously described (Charlton and Mack, 1994). Briefly, each rat was anesthetized with 400 mg/kg of chloral hydrate. A stainless steel guide cannula was stereotaxically placed 1.5 mm lateral and 0.6 mm caudal to the Bregma with the tip extended to the inner surface of the cranium, above the dura mater. At least 2 days following cannulation, injections were made through the cannula into the lateral ventricle with a 26 gauge insertion cannula, pre-measured to descend 5 mm from the surface of the skull into the lateral ventricle. Each injected rat was put in a cage which was then placed on the sensor assembly of the Tremor-Scan Monitor. The recording parameters were set according to the manufacturer's instructions by adjusting the Gain on the instrument to 4 which insured that most of the signals with large or small amplitudes remained within the detection limit or not reduced to the baseline respectively, as viewed on the computer monitoring screen. The noise that could interfere with the SAM-induced tremors is usually of low amplitude and was reduced to baseline levels by this gain setting. This setting was used for all subsequent recording and storage of the vibration signals due to tremor-like activities of the

TABLE 1

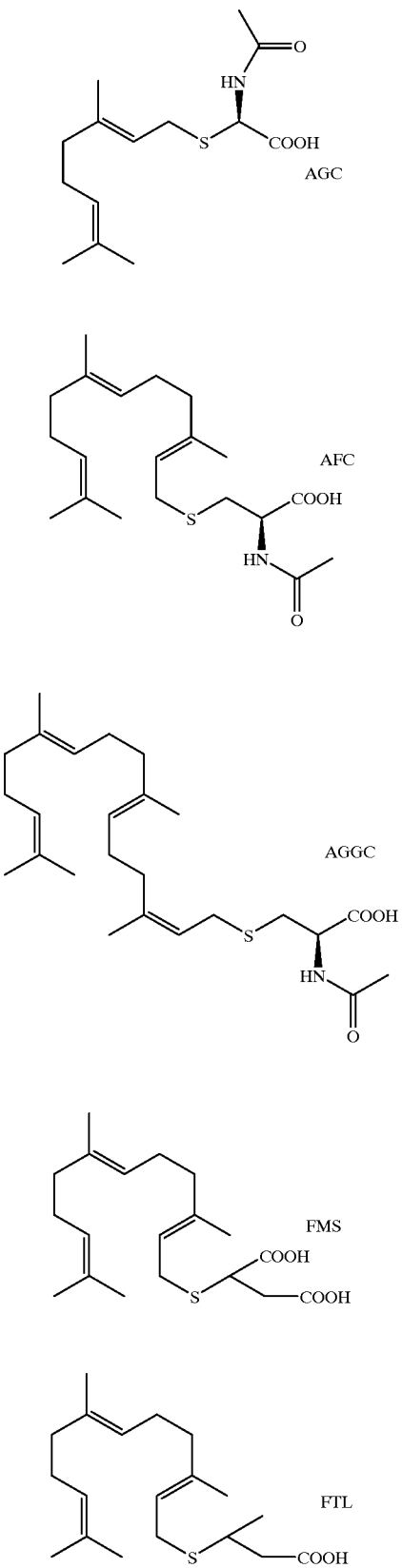

TABLE 1-continued

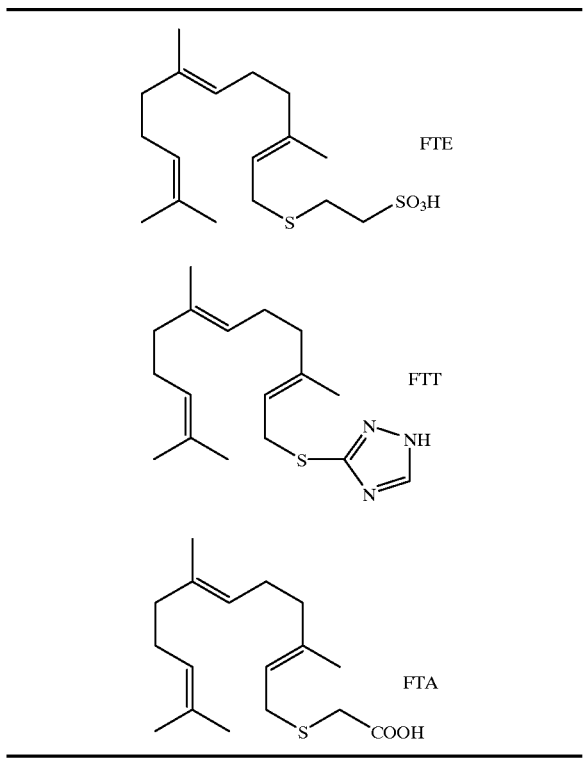

SAM-injected animals as well as the random movement activities of the control animals.

The Tremor Monitor software, which allows for the determination of 1) the signal amplitude, 2) the number of cycles in each activity or episode, 3) the number of activities and 4) the duration of each activity or episode, aided in the storage and subsequent retrieval and analysis of the recorded activity profiles. Analysis of the stored data was achieved by altering the minimum and maximum frequency, amplitude and number of cycles to reflect the unique properties of each kind of movement and thus delineate the SAM-induced tremors from non-tremor activity signals.

Dose Dependence of SAM-induced tremors

The dose-dependent effects of SAM was also determined in cannulated rats injected with 0 (PBS), 0.5, 0.75 and 1.0 mmmol of SAM. Their tremor activities were recorded on the Tremor-Scan monitor for 20 min.

Time-Dependence of SAM-induced Tremors

To determine the duration and magnitude of SAM-induced tremors, groups of cannulated rats were injected either with 1 mmmol of SAM or with 5 mml of PBS, as control. The animals were monitored on the Tremor-Scan Monitor for a duration of 2 h starting immediately after the injections.

Effect of L-DOPA, SAH and NADA on SAM-induced Tremors

Cannulated rats were injected either with PBS (5 mml), L-DOPA (1.5 mmmol), SAH (1.0 mmmol) or NADA (1.0 mmmol) followed by an injection of either 0.75 or 1.0 mmmol of SAM. Each compound was dissolved or finely suspended in PBS. They were then monitored for tremors on the Tremor Monitor for a period of 20 min.

In vitro association of [$^3$H-methyl]SAM With Rat Nerve Cell Membranes

Rat brain (1.76 g) was homogenized in 20 ml of 50 mM Tris-HCl, pH 7.4 containing 2.5 mM EDTA and 0.02% bovine serum albumin and centrifuged at 900×g for 10 min. The supernatant was transferred and the pellet re-suspended in the same buffer and centrifuged. The 900×g supernatants were combined and centrifuged at 20,000×g for 40 min. The supernatant was removed and the pellet resuspended in 5 ml of buffer, aliquoted and frozen at −70° C. until needed.

To understand whether the behavioral effects of SAM were due to interactions with cellular macromecules, [$^3$H-methyl]SAM (0.2 mmCi) was incubated with rat nerve cell membranes (30 mmg of protein) at 37° C. At the appropriate incubation periods, the reaction tubes were removed and centrifuged (13,000 rpm, MSE Centaur) for 10 min. The supernatant was discarded and the pellet suspended in scintillation fluid and their total radioactive content determined by scintillation counting.

Labeling and Extraction of Methylated Products

At least 2 days following cannulation, rats were injected with 10 mmCi of [$^3$H-methyl]-SAM in PBS over a 20 min period. This was followed by an immediate injection of SAM (2 mmmol) dissolved in PBS to induce tremors. The rats were sacrificed and the brains removed over ice and quickly homogenized in ice-cold PBS (2 ml/g of tissue, Polysciences Model X520). These were centrifuged at 25,000×g (Beckman J2-MC Centrifuge, JA-20 rotor) for 30 min. The supernatants were kept frozen for subsequent analysis while the pellet was resuspended in PBS and centrifuged as before. The supernatant was removed and the pellet resuspended in PBS containing 1% Triton X-100, agitated on ice for 1 h and centrifuged as before. The soluble fraction (Triton X-100 extract) was frozen for subsequent analysis.

Gel-Filtration Analysis

A 5 ml aliquot of the supernatant (130 mg of protein) and the Triton X-100 extract (180 mg of protein) containing $^3$H-methyl-labeled molecules were separated on Sephacryl S-100-HR (Pharmacia Biotech, Upssala, Sweden) packed in an XK 16/100 FPLC column (Pharmacia, 1.6 cm ID by 100 cm, 195 ml) that had been equilibrated with 20 mM Na$_3$PO$_4$, pH 7.4 containing 0.1% Triton X-100 and 0.2 M NaCl (buffer A). Identical amounts of the supernatant and Triton X-100 extracts were treated with 6 M guanidine HCl prior to analysis by gel-filtration chromatography. Elution was achieved with buffer A pumped at a flow rate of 2 ml/min by an LKB 2150 HPLC pump. Aliquots (100 mml) of the 4 ml fractions obtained from each chromatographic run were analyzed for radioactivity by scintillation counting.

Determination of Carboxyl Methyl Esters

The procedure was adapted from that of Philips et al (1993). Essentially, 100 mml aliquots of fractions 16, 38 and 42 of the native and denatured runs of both the supernatant and the membrane extracts were lyophilyzed in microcentrifuge tubes. NaOH (50 mml, 1 M) was then added and the open tubes placed in scintillation vials containing scintillation fluid, taking care not to spill the contents of the microcentrifuge tube into the scintillation vial. The vials were capped and incubated at 37° C. overnight so that labile radiolabeled methyl esters could be hydrolyzed to yield $^3$H-methanol that would evaporate from the microcentrifuge tubes into the scintillation fluid.

Methylation of FC Analogs

AFC, FTP and FTS (200 mmM) were each incubated for 60 min with rat brain membranes (240 mmg of protein) at 37° C. in 100 mM Tris-HCl, pH 7.4 containing SAM (10 mmM, 1.3 mmCi [$^3$H-methyl]-SAM), 5 mM MgSO$_4$ and 0.1 M NaCl in a total incubation volume of 400 mml. The reactions were stopped with 5% TFA and chilled on ice. Hexane (400 mml) was added and the contents of the tubes mixed thoroughly. This was followed by centrifugation at 20,000 g for 2 min. The upper hexane layer was removed and 250 mml analyzed by reversed-phase HPLC on a Whatman column (C18, 4.6×150 mm). Methylated FC analogs were eluted from the column at a rate of 1 ml/min with a 0 to 100% gradient of acetonitrile in 0.1% TFA from the $3^{rd}$ to the $15^{th}$ min of each run. This composition was maintained for a further 2 min before re-equilibration of the column for the next sample. Detection was conducted with an online radiochromatographic detection system (INUS β-ram, Tampa, Fla.).

Effect of Farnesylcysteine Analogs on SAM-Induced Tremors

AFC, FTP and FTS were each suspended in PBS and dissolved by adjusting the pH to 7.4 with NaOH followed by the addition of more PBS to make 0.2 mmol/ml solutions. PBS or each compound, dissolved in 5 mml of solution, was injected into the lateral ventricle of cannulated rats 5 min prior to SAM injections. SAM (1 mmmol in 5 mml of PBS) was injected and the movements recorded over a 20 min period as described above.

Effect of Farnesylcysteine Analogs on the Movements of Rats

Cannulated rats were injected (icv) with AFC or FTP (1 mmmol, 5 mml) in combination with PBS or 1 mmmol of SAM, injected similarly 5 min after injection of the FC analogs. Their movements were measured in an Animal Activity Monitor (AccuScan Electronics, Inc., Columbus, Ohio) and compared to those of control animals that received PBS.

Effect of Farnesylcysteine Analogs on Amphetamine-induced Rotation of 6-hydroxydopamine-lesioned Rats Lesions were induced on the left striatum by injecting with 6-OHDA (32 mmg, 10 mmg/mml) 0.7 mm anterior and 2.8 mm lateral relative to the Bregma and 5 mm into the cranium at a rate of 1 mml/min. The rats were then cannulated for subsequent injections into either the left or right lateral ventricle of the brain as stated earlier. One week after intra-striatal injections of 6-OHDA, the animals received an intraperitoneal (ip) injection of either PBS or amphetamine (5 mg/ml in PBS, 5 mg/kg). The same animals also received PBS or AFC (1 mmmol in 5 mml of PBS) delivered either into the left or the right lateral ventricle. The rotation of each animal was determined using the RotoScan Rotometer System (AccuScan Instruments, Inc., Columbus, Ohio).

Results

Characteristics of SAM-Induced Behavior

Although it has been shown previously that SAM induces tremors, hypokinesia, abnormal posture and rigidity in rats (Charlton, 1990, Charlton and Crowell, Jr., 1995; Crowell et al., 1993), a method for quantifying and characterizing the tremors had not been devised. In the present study, we consistently replicated physiological symptoms characteristic of PD in rats using the endogenous methyl donor, SAM. Normal behavioral activities such as grooming and raring that characterized the PBS-treated animals were never observed in SAM-treated rats until after recovery. Within about 0.5 to 2 min following injection with SAM, rats moved less, the limbs became stiff and spread out resulting in the animal lying on its ventral surface. The Straub tail phenomenon characterized by a stiff curled tail that depicts rigidity was a common feature. The rigidity of the SAM-treated animals was also assessed as previously done by placing the injected animals with the fore limbs on a pedestal (5). Animals suffering from rigidity typically spend over 2 min before moving off the object. Furthermore, the rats feel rigid to the touch. To calibrate the Tremor-Scan Monitor, a rat treated with 1 mmmol SAM and undergoing tremors was placed on the sensory assembly. A gain setting of 4 produced signals with the highest amplitude and minimal truncation at the tips when the animal was observed to be undergoing tremors. Only signals of intermediate amplitude, with no distinct pattern, were observed when the activity of rats treated with PBS and undergoing normal random movements were recorded (FIG. 1 panel A). As shown in FIG. 1 (panels B and C), the records for the SAM-injected rats showed distinct episodic cycles of high amplitude tremors punctuated by low amplitude signals characterizing hypokinesia, rigidity and abnormal posture. It is worth noting that although activity profiles with low amplitudes could also be recorded in control animals completely at rest, these were distinguishable from the SAM-treated animals since these were never in combination with any waves of high amplitude tremor signals. FIG. 1, Panels D-G show an identical region of an 11-, 21-, 31- and 41-fold condensed activity profile, respectively, revealing the wave characteristics of the tremor.

Figure 2:
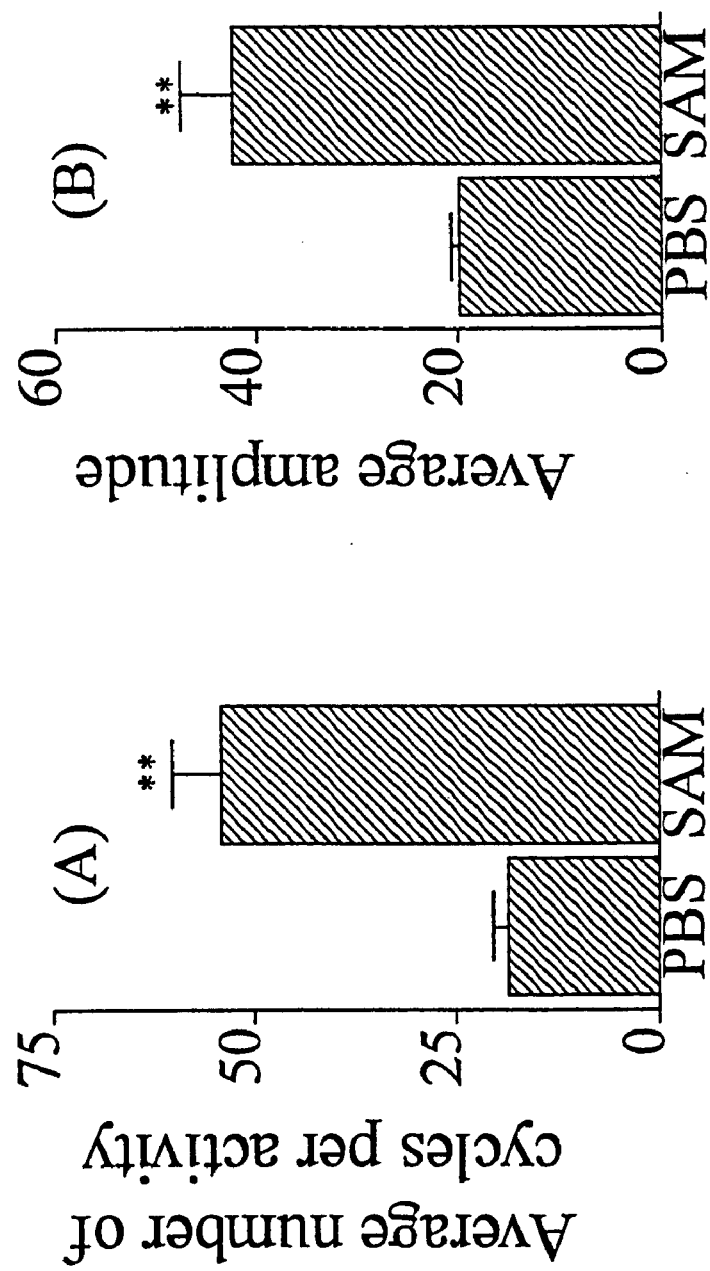
FIGS. 2(A and B): Characteristic movement differences between PBS- and SAM-treated rats. Twenty min activity profiles recorded and stored immediately following injection were analyzed with parameters set at 8, 20, 10, 10, respectively for minimum and maximum frequency, minimum amplitude and minimum number of cycles (waves) so as to register the maximum number and duration of the observed tremors in the SAM-treated animals. Analysis of the recorded data from the control (PBS) and treated (SAM) animals yielded on average distinctly different number of cycles per tremor (A) and amplitude (B), **$P<0.01$ by unpaired t-test. The results are the means±S.E.M., N=4.
Figure 2:
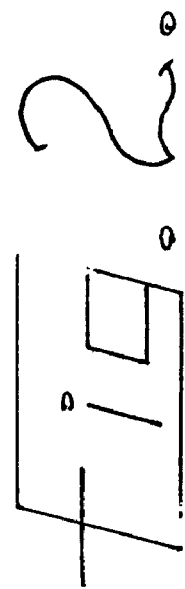
Figure 3:
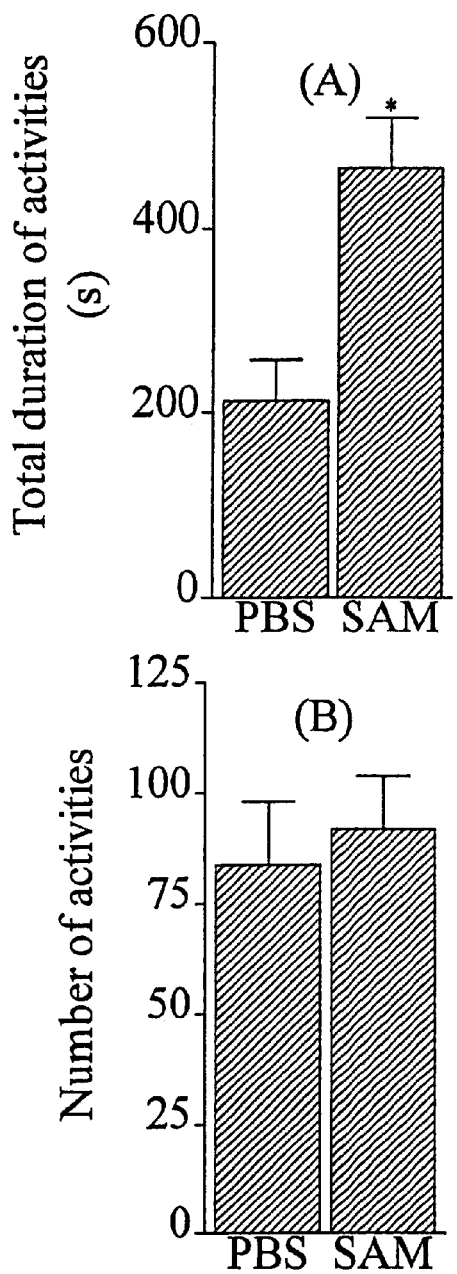
FIGS. 3(A–D): Total duration and number of tremors. The recorded data for the animals described for FIG. 2 when analyzed with minimum and maximum frequencies, amplitude and minimum number of cycles (waves) per tremor set at 8, 20, 10 and 10 respectively (A and B) or 8, 20, 20, 20 to take into account the experimentally-derived typical differences between SAM and PBS-injected rats as described in FIG. 2(C and D), *$P<0.05$, ***$P<0.001$ by unpaired t-test. The results are the means±S.E.M., N=4.
Figure 3:
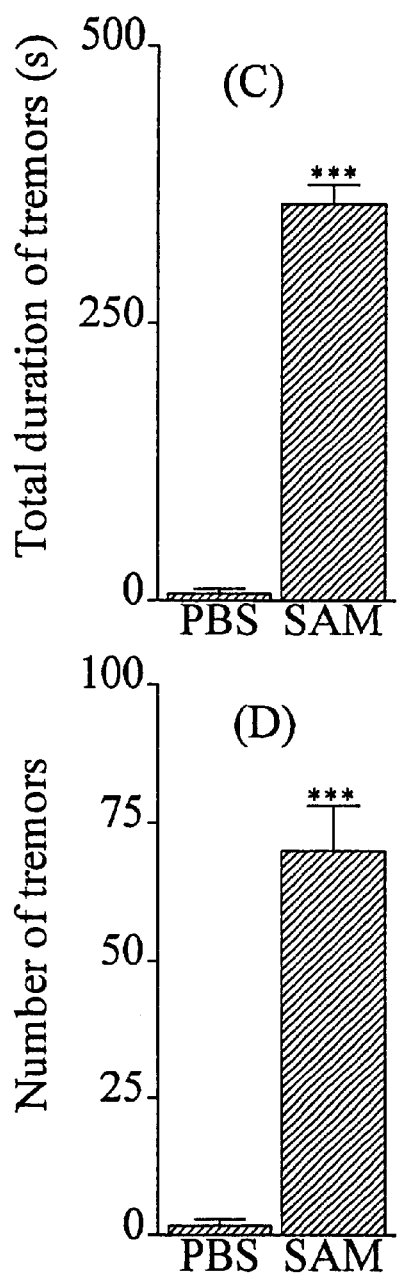

Raw data were obtained by combining the analysis parameters to insure the registration of most of the tremors in the recordings from SAM-treated animals. For this initial analysis, a frequency window of 8 to 20, minimum amplitude of 10 and a minimum of 10 cycles per activity or episode were employed. Although tremors were never observed in PBS-treated animals, activity was registered in the recordings of both SAM- and PBS-treated rats. However, a comparison between these raw sets of data for the SAM- and the PBS-treated rats revealed significant differences. The PBS-treated animals displayed a lower number of cycles (waves) per activity, 19±2 compared to 54±6 for the SAM-injected animals (FIG. 2A). The average amplitude for both groups followed a similar pattern, 19.8±1 and 42.3±5 for the PBS- and SAM-treated rats, respectively (FIG. 2b). Similar frequencies were observed when recordings of PBS-treated (11±0.2) and SAM-treated (12±0.1) animals were analyzed. The raw data show that SAM-treated rats underwent tremors for a total duration of 470±50 sec within the 20 min monitoring period whereas the PBS-treated animals underwent activities lasting 210±50 sec (FIG. 3, A). The number of activities measured, however, was not significantly different for both groups, being 84±14 for the PBS-injected rats and 92±12 for the SAM-treated rats (FIG. 3B). Thus non-tremor related activities of control animals were also detected using the minimum amplitude and minimum cycles per activity of 10. These non-tremor activities were eliminated when the experimentally-derived values (illustrated in FIG. 2) of 20 for both the minimum amplitude and cycles per activity was used in re-analyzing the recorded data. These parameters registered most of the tremor activity in the recordings of the SAM-treated rats (360±18 sec) and almost none in the PBS controls (6±4 sec, FIG. 3C). Similarly, the number of tremor activities exhibited by the SAM-treated group was 70±8 as compared to only 2±1 detected for the PBS controls (FIG. 3D). It is worth noting that these more stringent analysis criteria underestimated the number and duration of the tremors since tremor signals with amplitudes and number of cycles of less than 20 were eliminated from the data of the SAM-treated animals. The activities with amplitudes above 20 were practically nonexistent in the control animals. We observed that the activities recorded in the PBS-treated animals were in fact due to random movements and grooming.

Dose-Dependence of SAM-induced Tremors

Figure 4:
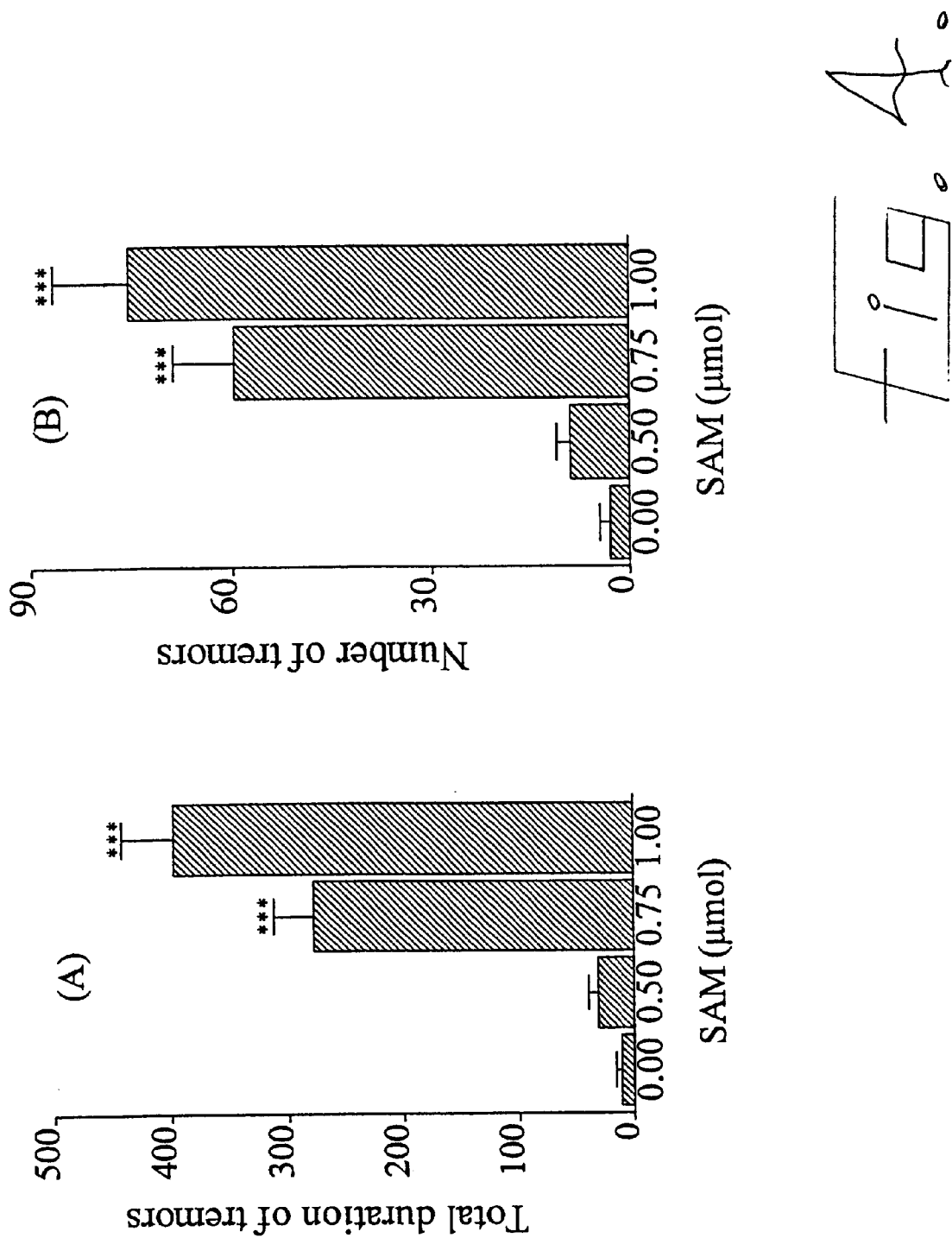
FIGS. 4(A and B): Dose-dependence of SAM-induced tremors. Cannulated rats were injected either with PBS or varying doses of SAM and all movements recorded for the following 20 min. Data analysis with minimum and maximum frequencies, minimum amplitude and minimum number of cycles (waves) per tremor set at 8, 20, 20 and 20, respectively, revealed that the total duration (A) and number of tremors (B) both increased with increasing doses of SAM injected between 0.5 and 1 mmol, ***$P<0.001$ when compared to PBS controls by unpaired t-test. The results are the means±S.E.M., N=4.

SAM induced tremors in a dose-dependent manner, showing a steep dose-response for both the number and duration of tremors. The total duration of tremors was minimal when rats were injected with 0.5 mmmol of SAM but increased 9- and 12-fold when injected with 0.75 and 1 mmmol of SAM, respectively, as compared to the 0.5 mmmol injection (FIG. 4A). The number of tremors recorded was minimal when rats were injected with 0.5 mmmol of SAM but increased 7- and 8-fold when the rats were injected with 0.75 and 1 mmmol of SAM, respectively (FIG. 4B). This disproportionate increase in the duration and number of tremors when the dose of SAM was increased indicates that higher doses increased not only the number but also the duration of the episodes.

Time-Dependence of SAM-induced Tremors

Figure 5:
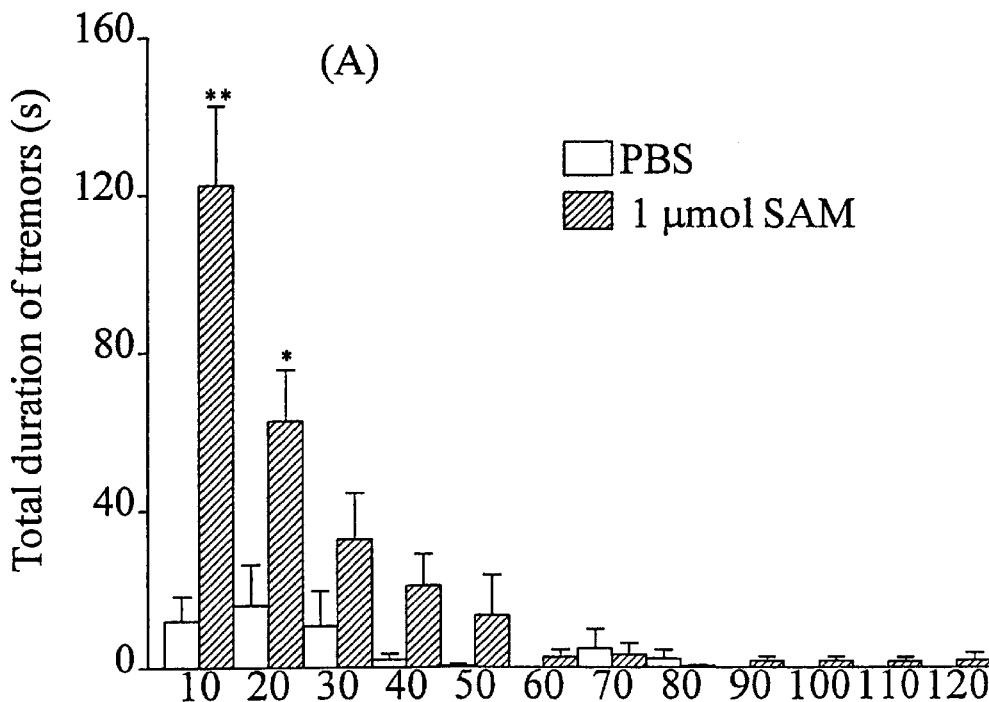
FIGS. 5(A and B): Time-dependence of SAM-induced tremors. Cannulated rats were injected either with PBS or SAM and their movements recorded over a 2 h period. The total duration (A) and number of tremors (B) for successive 10 min intervals were computed using the same parameters as in FIG. 4, *$P<0.05$, **$P<0.01$ when compared to PBS controls for the respective time interval by unpaired t-test. The results are the means±S.E.M., N=7.
Figure 5:
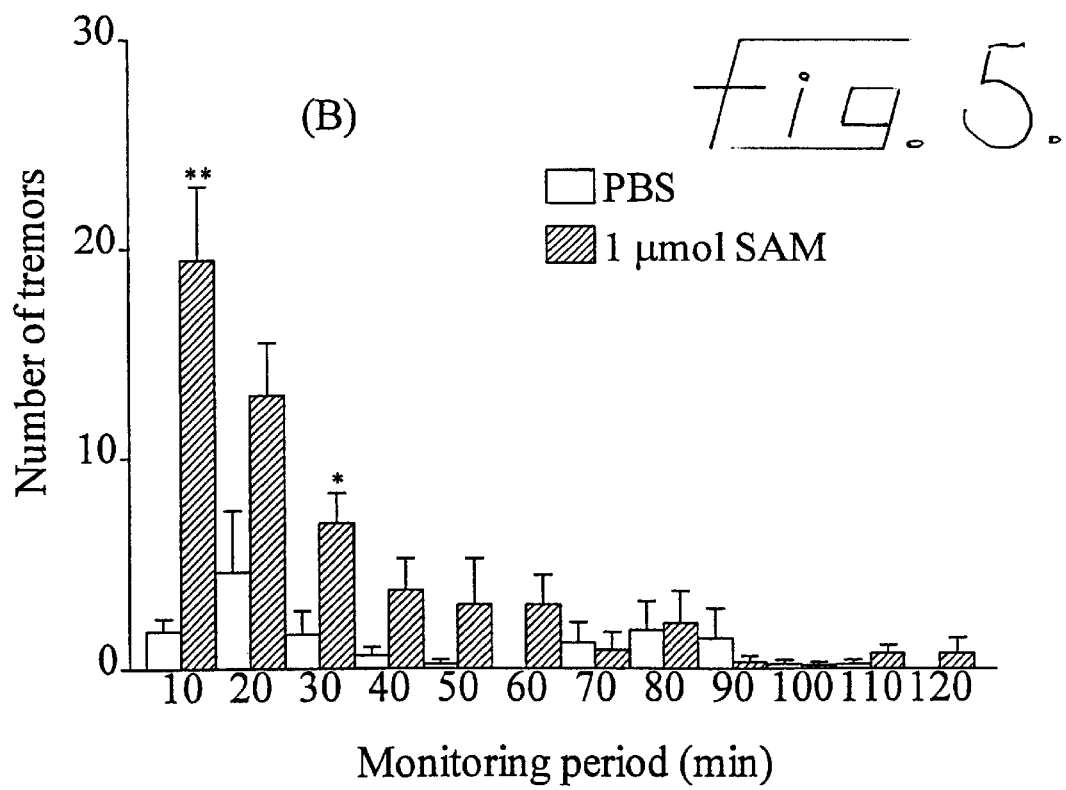

A 1 mmmol dose of SAM or PBS was administered to rats and their activities recorded over a 2 h period. The data was analyzed as stated above and the total duration and number of tremors occurring within successive 10 min intervals following injection were registered. The total duration of tremors peaked within the first 10 min accounting for a fifth of the recording period (120±20 sec). In the successive 10 min periods, the total time that the rats underwent tremors declined in a first order fashion (FIG. 5A). As shown in FIG. 5B, the highest number of tremor episodes occurred during the first 10 min, at a rate of about 2 episodes per min. The number of tremors decreased in a first order fashion from the first 10 min interval value of 19±4. The background noise seen in the control rats is apparently due to rapid and active grooming soon after handling. Although the severity of the tremors was almost reduced to control levels within 40 to 50 min following injection, abnormal posture, hypokinesia and rigidity remained a characteristic feature for about 90 min. The recovery usually commenced with a gradual increase in mobility coupled with gradual raising of the ventral surface from the floor of the cage as the rigidity decreased and the animals regained their normal posture.

Effect of L-DOPA, NADA and SAH on SAM-induced Tremors

Figure 6:
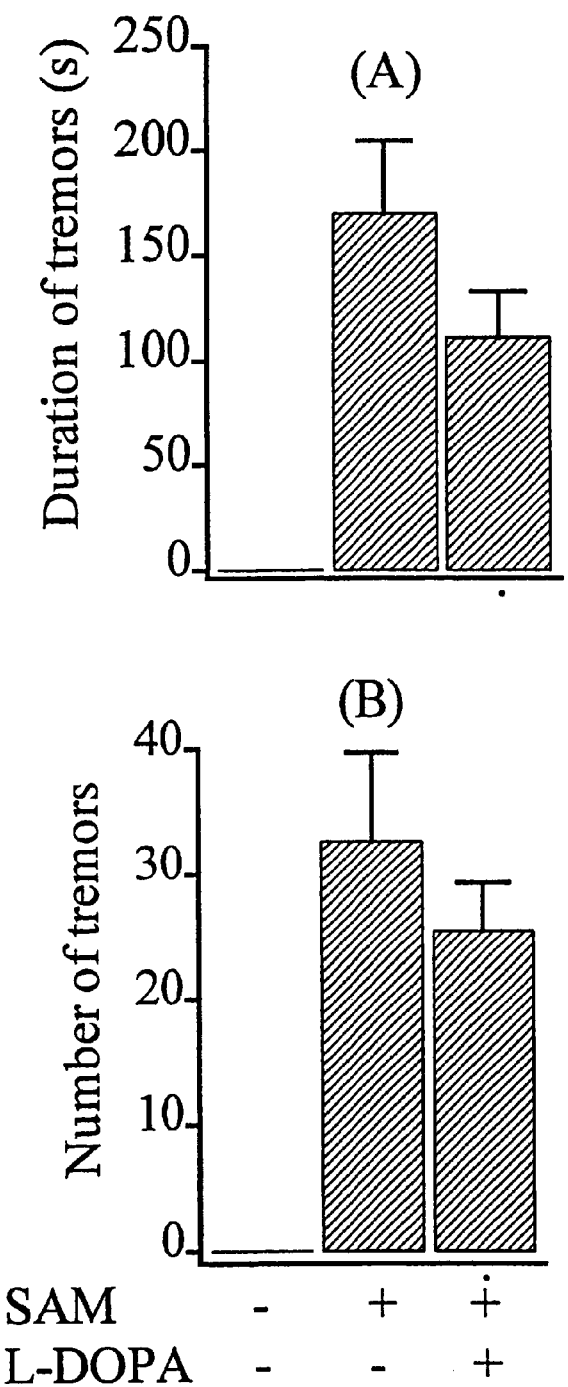
FIGS. 6(A and B): L-DOPA effect on the SAM-induced PD-like symptoms: Cannulated rats were injected icv with 1.5 mmol of L-DOPA 5 min before an injection of 0.75 mmol of SAM, each dissolved or suspended in 5 ml of PBS. Their movements were then recorded on a Tremor Monitor over a 20 min period. The total duration and number of tremors was analyzed as described in the methods section.
Figure 7:
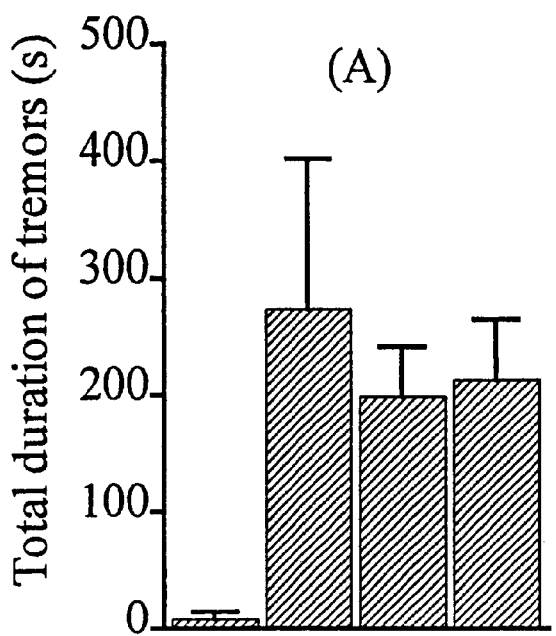
FIGS. 7(A and B): NADA and SAH effect on the SAM-induced PD-like symptoms: Cannulated rats were injected icv with 1 mmol of either NADA or SAH followed by 1 mmol of SAM, each compound dissolved or suspended in 5 ml of PBS. Their movements were then recorded on a Tremor Monitor over a 20 min period. The total duration and number of tremors was analyzed as described in the methods section.
Figure 7:
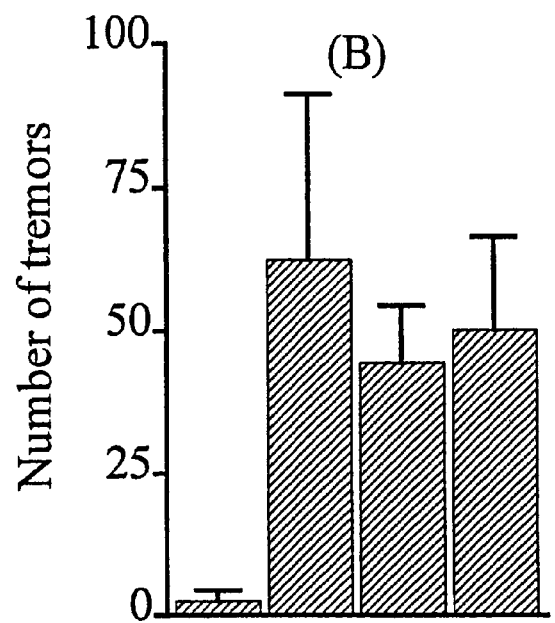
Figure 7:
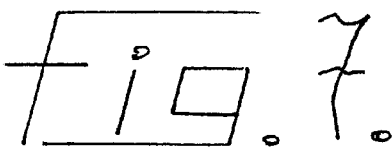

Injecting 1.5 mmmol of L-DOPA into the lateral ventricles of rats before administering 0.75 mmmol of SAM caused a small, though insignificant decrease in the number (25±4) and total duration of tremors (111±22) when compared to the SAM-treated animals (33±7 tremors averaging 170±34 s) when monitored for a 20 min period (FIG. 6). In a similar study, 63±±29, 45±±10 and 50±±16 tremors averaging 273±128, 200±43 and 212±52 were recorded for SAM, NADA and SAH over a 20 min period, respectively (FIG. 7).

Figure 8:
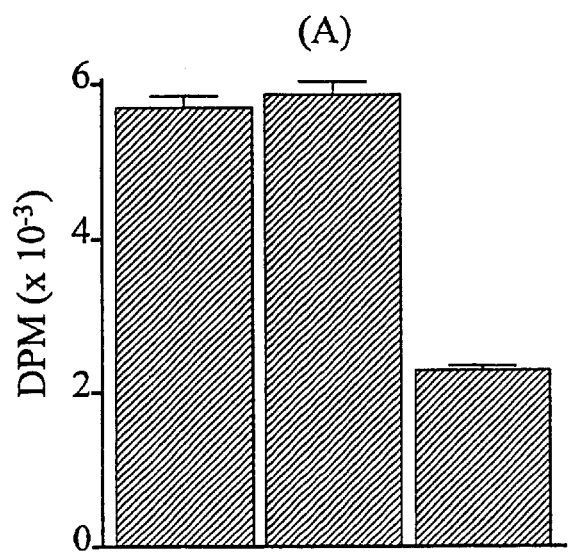
FIGS. 8(A and B): Association of [$^3$-methyl]SAM and $^3$H-MPP$^+$with rat nerve cell membranes: Rat nerve cell membranes (30 mg) were incubated either with 0.2 mCi of [$^3$H-methyl]SAM (A) or $^3$H-MPP$^+$(B) for 75 min in the presence or absence of non-radioactive 100 mM concentrations of SAH, MPP+ or SAM at as indicated. The samples were then processed for scintillation counting as described in the methods.
Figure 8:
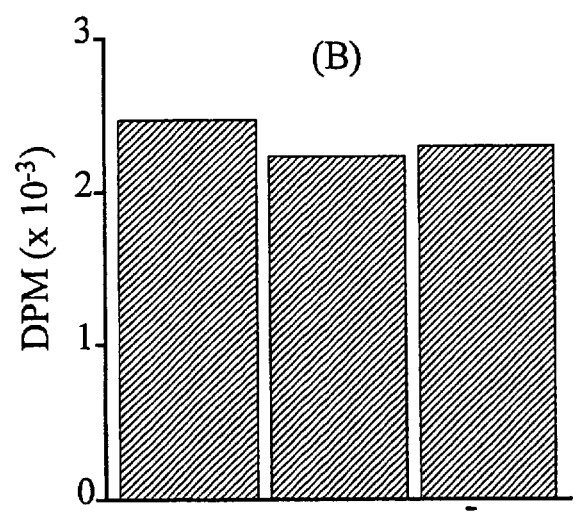
Figure 9:
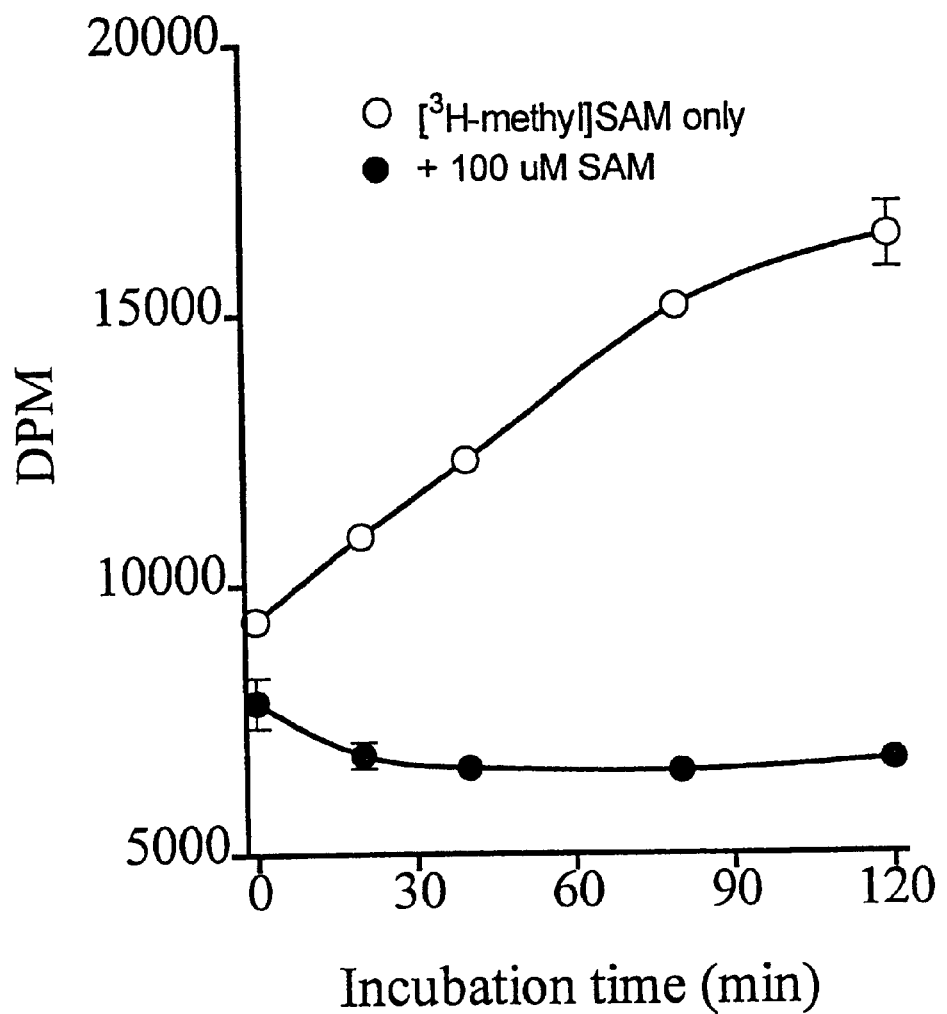
FIG. 9: Time-dependent association of [$^3$H-methyl]SAM with rat nerve cell membranes: Rat nerve cell membranes (30 mg) were incubated with [$^3$H-methyl]SAM for varying time periods in the presence (●) or absence (○) of 100 mM SAM as described in the methods. The different samples were processed for scintillation counting as described in the methods.
Figure 10:
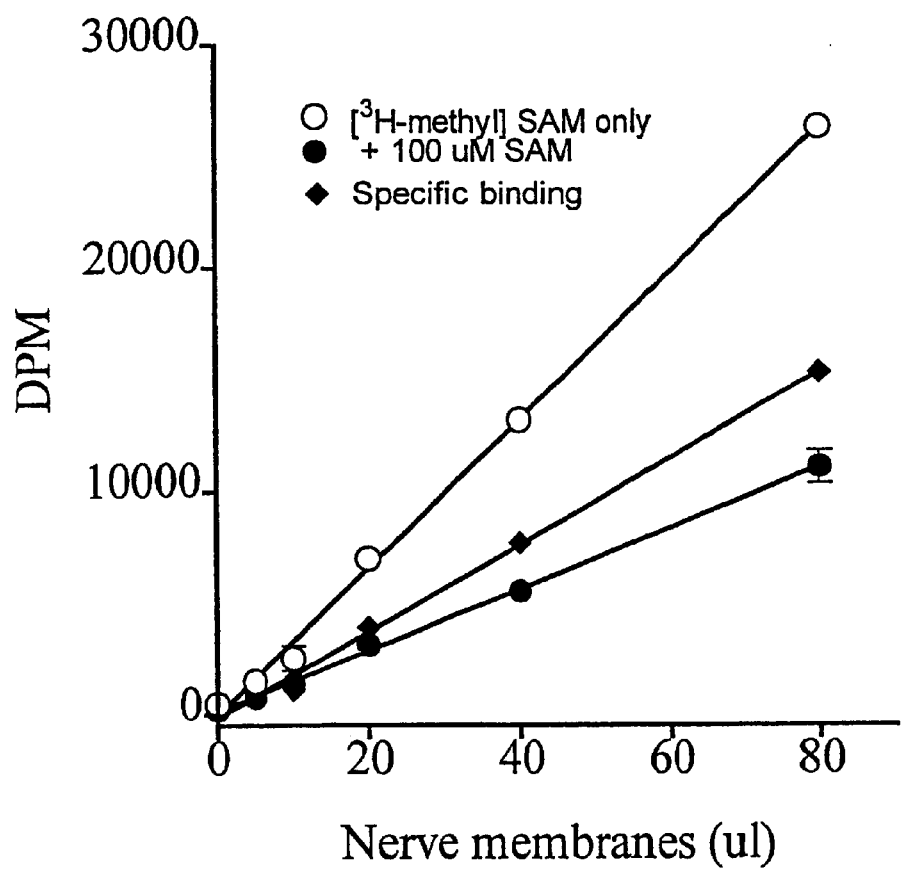
FIG. 10: Effect of varying amounts of rat nerve cell membranes on the association with [$^3$H-methyl]SAM: Rat nerve cell membranes (0–108 mg) were incubated with [$^3$H-methyl]SAM in the presence (●) or absence of (○) 100 mM of non-radioactive SAM for 60 min. The difference between the uninhibited and inhibited association was computed to give the specific interaction (♦).
Figure 11:
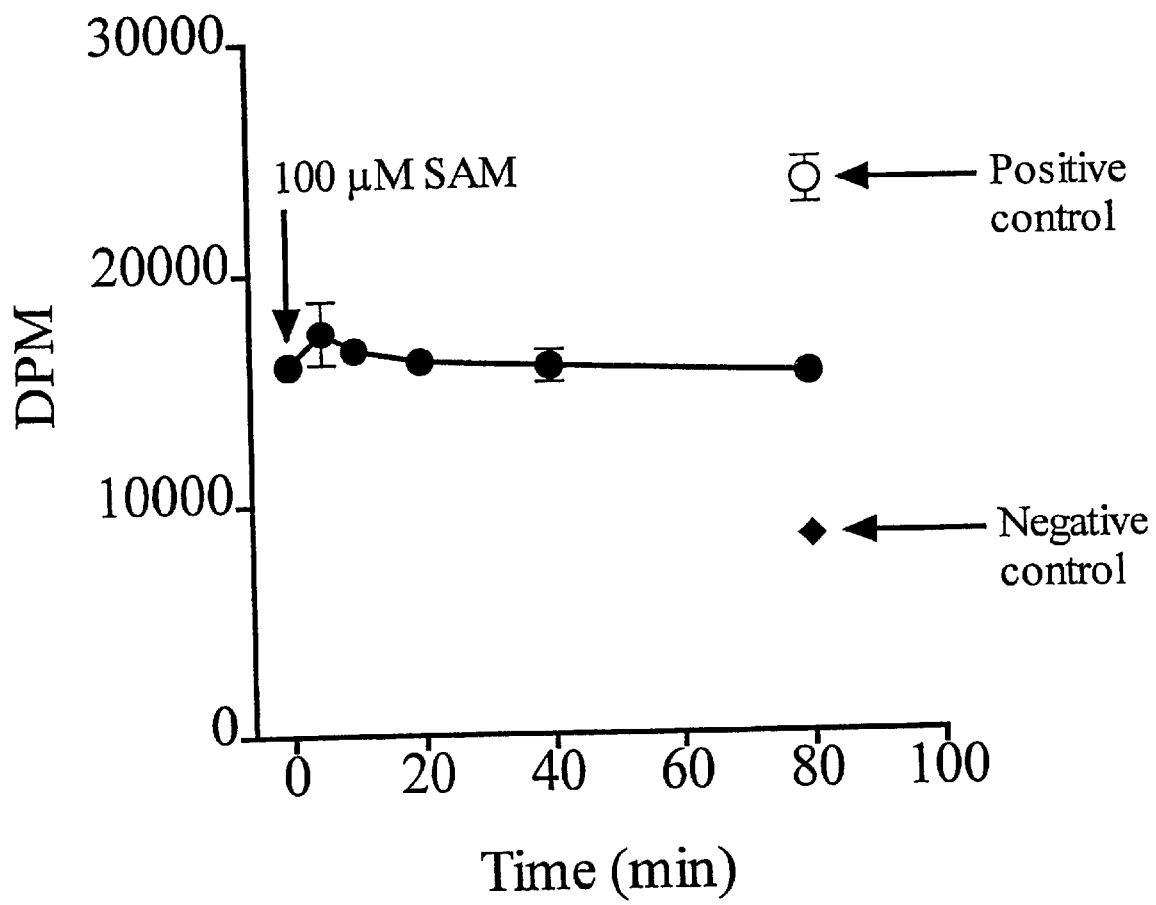
FIG. 11: Reversibility of the membrane-associated [3H-methyl]SAM: [3H-methyl]SAM was incubated with rat nerve cell membranes for 2 h. Non-radioactive SAM (100 mM) was then added followed by further incubation for varying periods of time. The samples were processed for scintillation counting to determine the residual membrane-associated radioactivity. Negative and positive controls represent samples which were either treated with 100 mM SAM at the beginning of the incubation or received no SAM throughout the incubation.

Effect of [$^3$H-methyl]SAM or $^3$H-MPP$^+$Incubation With Rat Nerve Cell Membranes When [$^3$H-methyl]SAM was incubated with rat nerve cell membrane preparation, a significant amount of radioactivity (about 6000 DPM) became associated with the membranes. This was reduced to about 2000 DPM if 100 mmM SAH was included in the incubation mixture (FIG. 8A). No effect on the association was observed in the presence of 100 mmM 1-methyl-4-phenylpyridinium ion (MPP$^+$). Incubating membranes with $^3$H-MPP$^+$revealed a total radioactive association of only about 2000 DPM. This was little affected by SAM or SAH (FIG. 8B). Incubating membranes with [$^3$H-methyl] SAM for varying time periods revealed a time-dependent incorporation of radioactivity. This was inhibited if 100 mmM non-radioactive SAM was included in the incubation mixture (FIG. 9). Radioactive association was found to bear a strong correlation with the amount of membranes used, increasing proportionately with increasing amounts of membranes (FIG. 10). Again, a significant portion of the association was proportionately inhibited by 100 mmM of non-radioactive SAM. To understand whether the radioactive association with the membranes is reversible, incubations were conducted for 2 h after which 100 mmM of non-radioactive SAM was added. This was then incubated for varying time periods, processed and analyzed for total radioactivity remaining in the membranes. As shown in FIG. 11, the amount of membrane-associated radioactivity neither increased nor decreased following the addition of non-radioactive SAM. At the same time, more radioactivity was incorporated into samples that were incubated similarly but did not receive the 100 mmM of non-radioactive SAM after 2 h (positive control). The radioactivity content of samples that received 100 mmM of non-radioactive SAM at the start of the incubation (negative control) remained significantly lower (FIG. 11).

In Vivo SAM-Dependent Methylation

Figure 12:
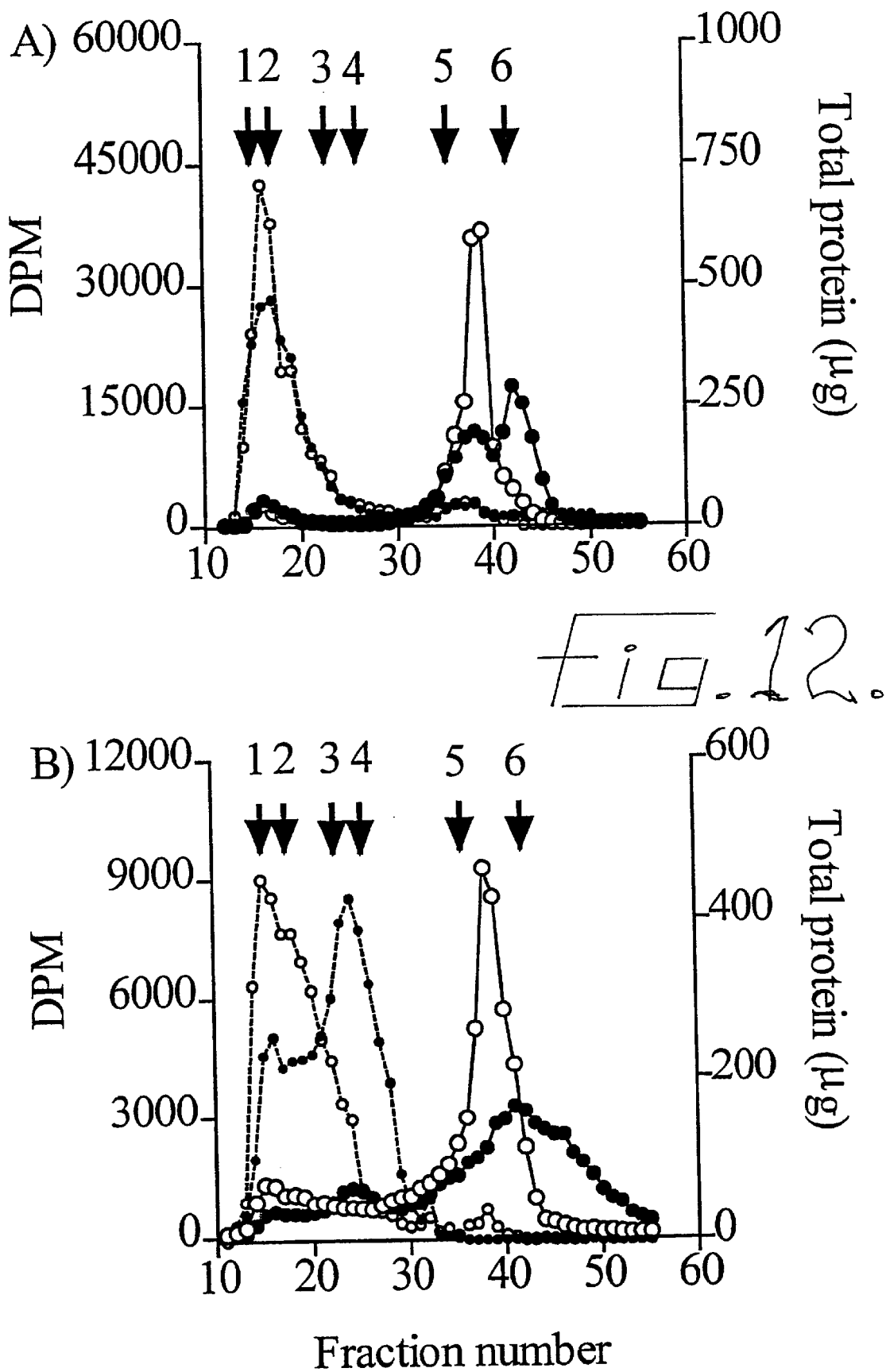
FIGS. 12(A and B): Methylation of cellular components: Rats were cannulated for subsequent injection into the lateral ventricle. In vivo labeling with S-[methyl-$^3$H]-SAM (10 mCi in PBS) followed by the preparation of brain supernatant and membrane extracts was as described in the methods. Aliquots of the supernatant (130 mg protein, panel A) and Triton X-100 membrane extract (180 mg of protein, panel B) were separated by gel-filtration chromatography. Chromatography was conducted either on the native samples (●) or aliquots that had been denatured by treatment with 6 M guanidine HCl (○). The radioactivity content (solid lines) and the total protein (dashed lines) of the eluted fractions was determined by scintillation counting and Bradford protein assay, respectively. The elution points of the molecular weight standards are denoted by the numbers 1: blue dextran, 2: BSA (66000), 3: carbonic anhydrase (29,000), 4: cytochrome C (12,400), 5: aprotinin (6,500) and 6: tyrosine (181).

To understand whether these behavioral changes could be due to biochemical alterations of macromolecular structures, cannulated rats were injected with radio-labeled SAM followed by extraction of brain tissue and analysis by gel-filtration chromatography as described in the methods section. As shown in FIG. 12A, scintillation counting of aliquots of the fractions obtained by gel-filtration analysis of a portion of the brain supernatant revealed two main peaks of radioactivity. One of these peaks eluted with an apparent molecular weight of 5 kDa while the second eluted with the total volume. One main peak that eluted with an apparent molecular weight of 5 kDa was observed when an equal amount of the brain supernatant was first treated with 6 M guanidine HCl before gel-filtration analysis. Analysis of the native Triton X-100 extract of the membranes revealed the presence of a single broad peak that extended beyond the total volume but centered around 5 kDa. However, denaturing with guanidine HCL before gel-filtration analysis resulted in a sharper peak with an apparent molecular weight value of around 5 kDa (FIG. 12B). Other minor methylation products with smaller elution volumes and therefore of higher apparent molecular masses were observed both in the supernatant and membrane fractions.

Detection of Carboxyl Methyl Esters in the Radioactive Peak Fractions

Figure 13:
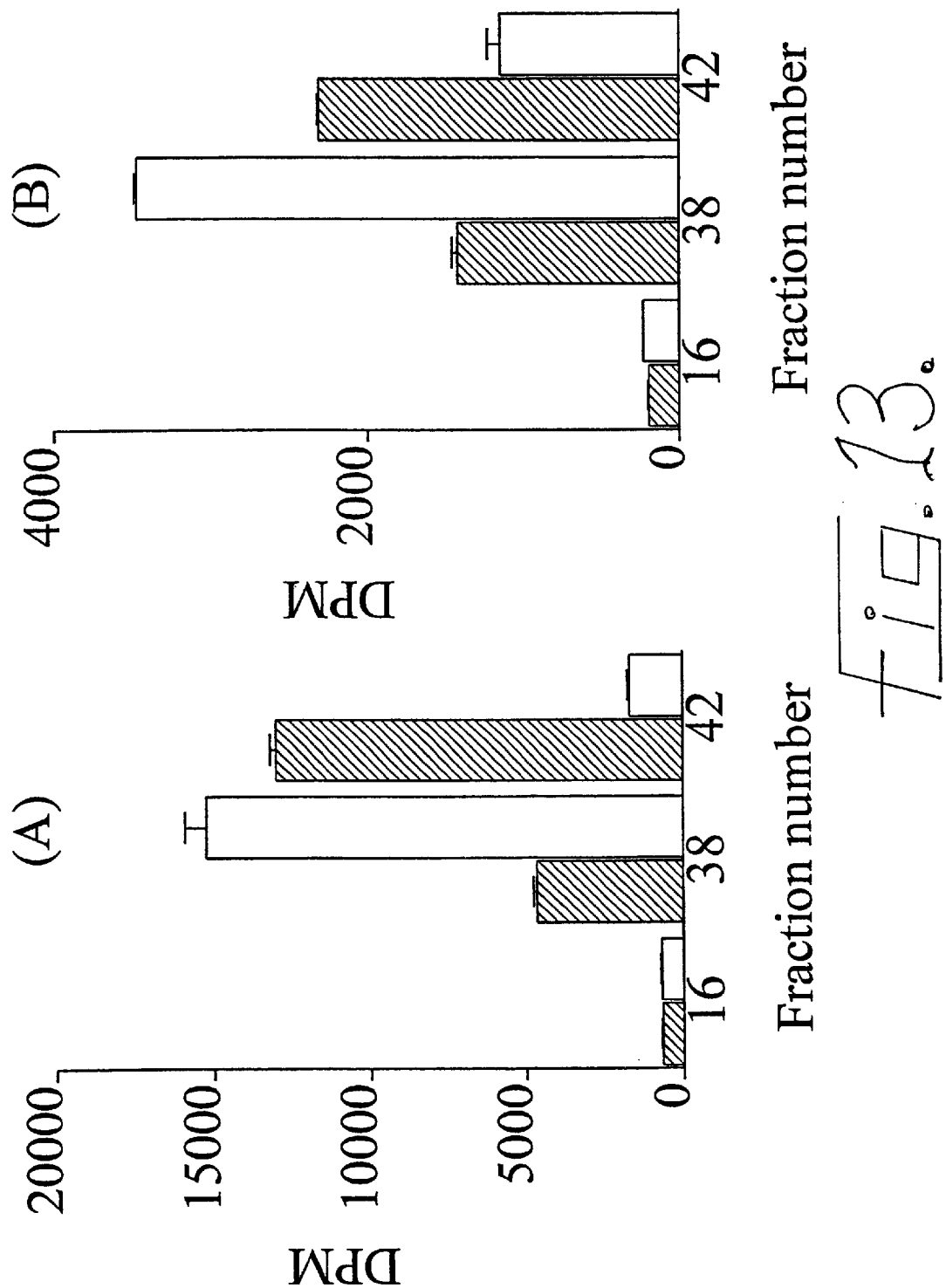
FIGS. 13(A and B): Carboxyl methyl esters in radioactive peak fractions. Aliquots (100 ml) of radioactivity peak fractions from the different chromatographic runs (FIG. 1) were lyophilized in micro-centrifuge tubes. NaOH (1 M, 50 ml) was added and each uncapped tube was placed into a scintillation vial containing scintillation fluid. The vials were capped and tubes incubated overnight at 37° C. so that volatile [$^3$H]-methyl groups could evaporate into the scintillation fluid. The volatilized radioactivity from the supernatant (panel A) and membrane extract (panel B) was determined by scintillation counting. Hatched and open bars represent fractions from the chromatographic runs using native and denatured samples, respectively (±S.E.M., N =3).

SAM-dependent methylation of carboxylic acid groups as occurs in proteins results in carboxyl methyl esters. These are base-labile and are thus hydrolyzed when incubated under basic conditions (Philips et al., 1991). To determine whether the peaks of radioactivity that eluted from the chromatographic column contained such esters, 100 mml aliquots of fractions 16, 38 and 42 of the native and denatured runs of both the supernatant and the membrane extracts were lyophilyzed in microcentrifuge tubes. Treatment of the lyophilized samples as described in the methods section followed by scintillation counting revealed that a significant portion of the labeled products were indeed carboxyl methyl esters (FIG. 13).

Methylation of FC Analogs

Figure 14:
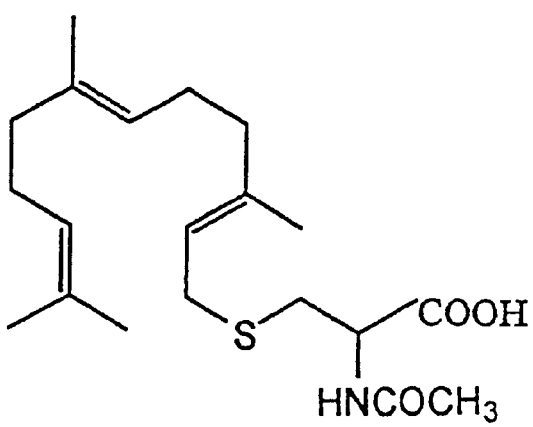
FIG. 14: FC analogs: Structures of AFC, FTP and FTS. [The structural integrity of the trans,trans-farnesyl group is important for specificity of function. Replacement of the trans,trans-farnesyl group with an all trans-geranylgeranyl or geranyl would increase or decrease pharmacological potency, respectively. Removal of the double bonds will tend to result in loss of activity. However, substitution of a hydrogen atom or methyl group by a halogen atom such as fluorine or chlorine is expected not to substantially affect pharmacological activity.]
Figure 14:
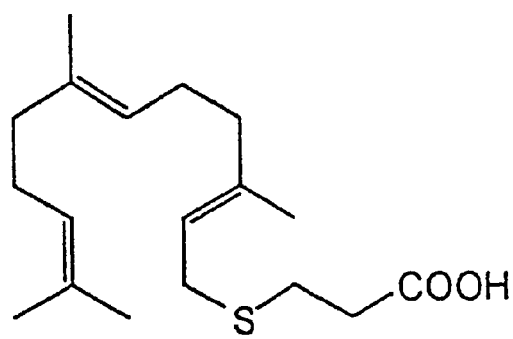
Figure 14:
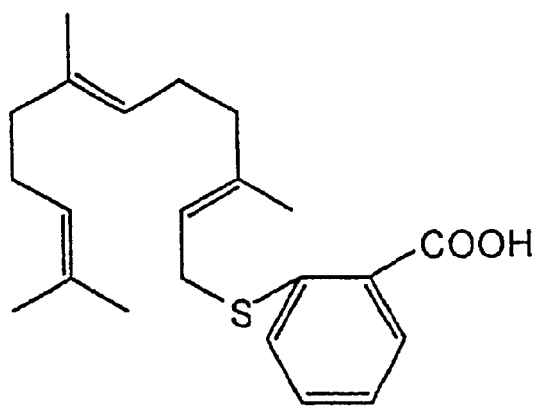
Figure 15:
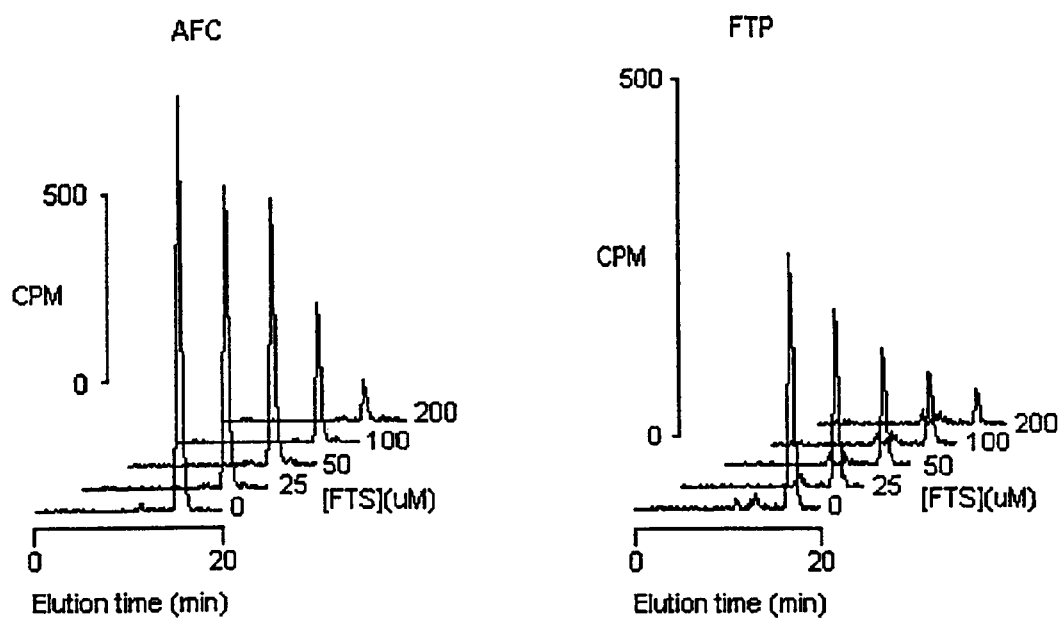
FIG. 15: SAM-dependent methylation of AFC and FTP by rat brain membranes: inhibition by FTS: AFC and FTP were incubated with [$^3$H-methyl]SAM, rat brain membranes (240 mg) and the indicated concentrations of FTS for 60 min under the conditions described in the methods section. Reactions were stopped with 5% TFA, the methylated FC analogs were extracted with hexane and analyzed by reversed-phase HPLC with online radiochromatographic detection.

Based on the above data, it was deemed possible that the SAM-induced symptoms could be as a result of excessive methylation of prenylated proteins. DA neurons are affected in PD and L-DOPA, a DA precursor, is used to remedy effects of PD. DA neurotransmission is through DA receptors that function in association with trimeric G-proteins, the γ-subunits of which are prenylated, range in size between 5 and 7 kDa (Cali et al, 1992) and are capable of undergoing reversible C-terminal carboxylmethylation. The fact that some of the in vivo methylated peaks were around 5 kDa and gave off volatile radioactive groups in basic medium suggested the presence of carboxyl methyl esters. For this reason, AFC, FTP and FTS (FIG. 14), which chemically and functionally mimic the C-terminal prenylated portion of the Gγ-subunit, were synthesized. AFC and FTP were shown to be avid methyl acceptors when incubated with rat nerve cell membranes in the presence of [$^3$H-methyl]SAM. Although FTS was never methylated, it dose-dependently inhibited the methylation process (FIG. 15).

Effect of Farnesylcysteine Analogs on SAM-Induced PD-like Symptoms

Figure 16:
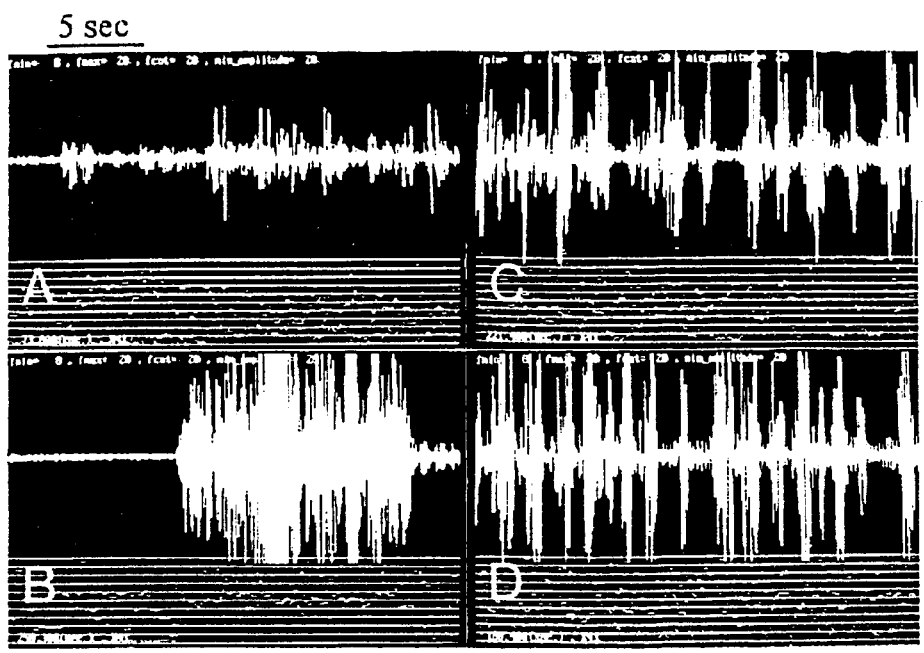
FIGS. 16(A–D): Sections of recorded movements of treated rats. Rats were cannulated as described in the methods section. At least two days after cannulation, rats were either treated with PBS alone (panel A), PBS followed 5 min later by 1 mmol of SAM (panel B), 1 mmol of AFC followed 5 min later by 1 mmol of SAM (panel C) or 1 mmol of FTP followed 5 min later by 1 mmol of SAM.

When SAM was injected into the lateral ventricle of cannulated rats, tremors, hypokinesia, rigidity and abnormal posture were routinely observed within 0.5–2 min of injection. On the contrary, PBS-treated rats showed no behavioral changes and activity recordings on the Tremor Monitor revealed patterns characteristic of random movement and grooming. As shown in FIG. 16 (panel A), only low amplitude signals were often recorded. The onset of tremors in the SAM-treated animals was often preceded by rigidity of the legs and thighs, spreading of the limbs and assumption of a posture that rested the abdomen on the floor of the cage. Tremor Monitor recordings of this activity showed characteristic patterns marked by periods of low/baseline amplitude punctuated by high amplitude signals (FIG. 16, panel B). The low amplitude signals were background signals characteristic of the periods without tremors, with the animal displaying severe rigidity, hypokinesia and abnormal posture while the high amplitudes were associated with tremor episodes.

This behavior observed in SAM-treated animals was completely abolished if the animals were injected with 1 mmmol each of prenylcysteine analog 5 min before the injection of SAM. In this case, the animals embarked on an unusually high level of activity, rushing from one side of the cage to the other. Activity recordings of these animals whose treatment with SAM was preceded with AFC (FIG. 16, panel C) or FTP (FIG. 16, panel D) both displayed a unique characteristic that resembled neither that of the PBS-only nor the SAM-only-treated rats. The repeated cycles of high amplitude alternating with low amplitude signals depict 'runs' followed by 'stops' as the animals rushed from one side of the cage to the other. This kind of activity was observed in over 70% of the animals studied while the remainder appeared normal, displaying neither PD-like symptoms nor hyperactivity.

Figure 17:
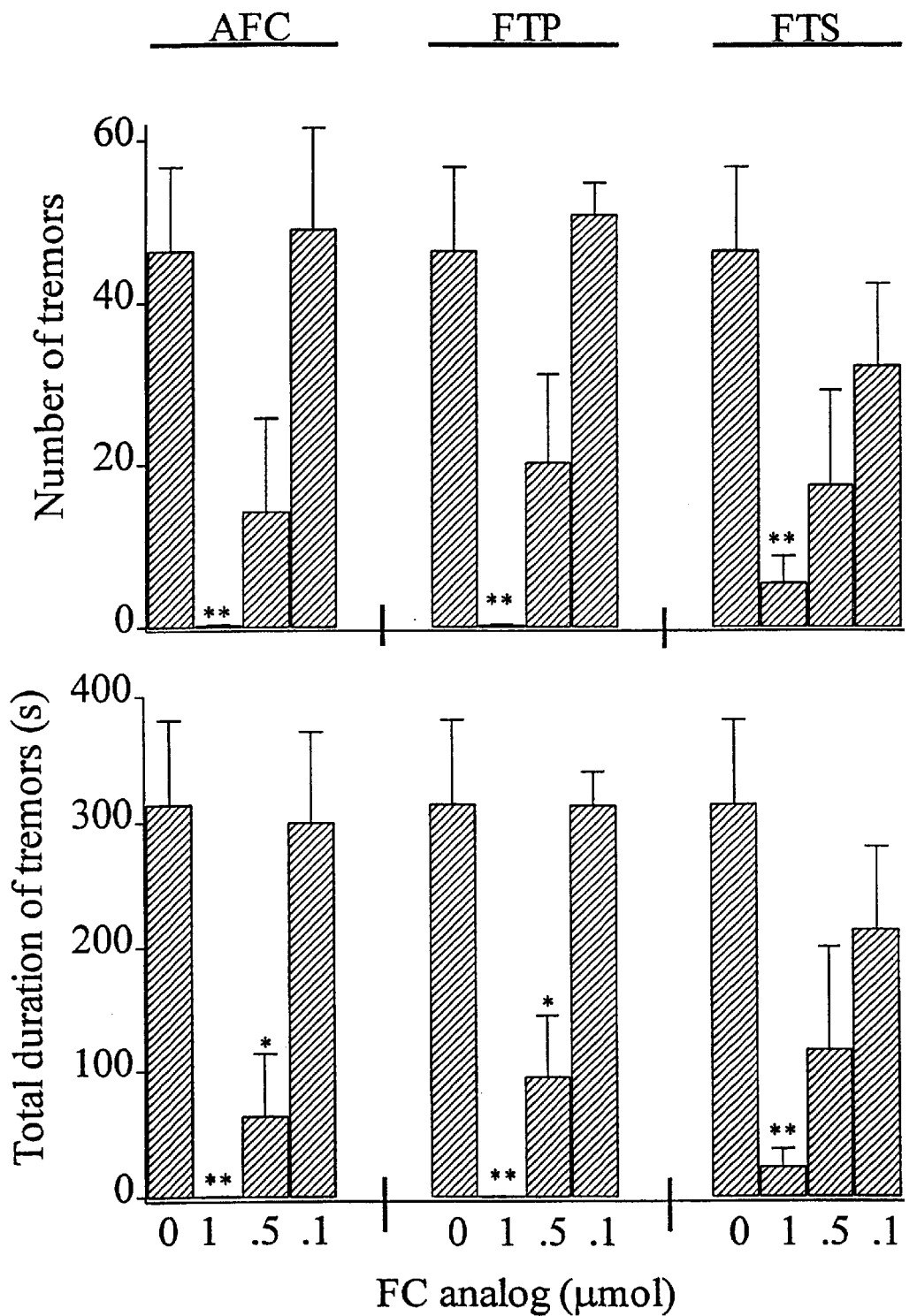
FIG. 17: FC analogs inhibit SAM-induced tremors. Cannulated rats were injected icv with the indicated of doses of the respective FC analogs. Five minutes later, 1 mmol of SAM was administered and the movements of each animal recorded on the Tremor Monitor for 20 min. All animals were observed for tremors and the recorded data for those underwent tremors was then analyzed for the number (panel A) and duration (panel B) of the tremors using previously established parameters. *$P<0.05$, **$P<0.001$ by unpaired t-test. The results are the means±S.E.M., N=6.

The tremor activity of rats treated with 0, 0.1, 0.5 and 1 mmmol of AFC, FTP or FTS followed by 1 mmmol of SAM was quantified over 20 min on the Tremor monitor. As shown in FIG. 17, control rats (0 mmmol FC analog) suffered on average 46±10 tremors lasting 310±70 seconds. On the contrary, no tremors were observed when rats were first treated with 1 mmmol of either AFC or FTP and significantly fewer tremors when FTS was administered. Reduced doses of FC analogs were less effective with significant reduction of tremors only afforded by 0.5 mmmol of AFC and FTP (FIG. 17).

Figure 20:
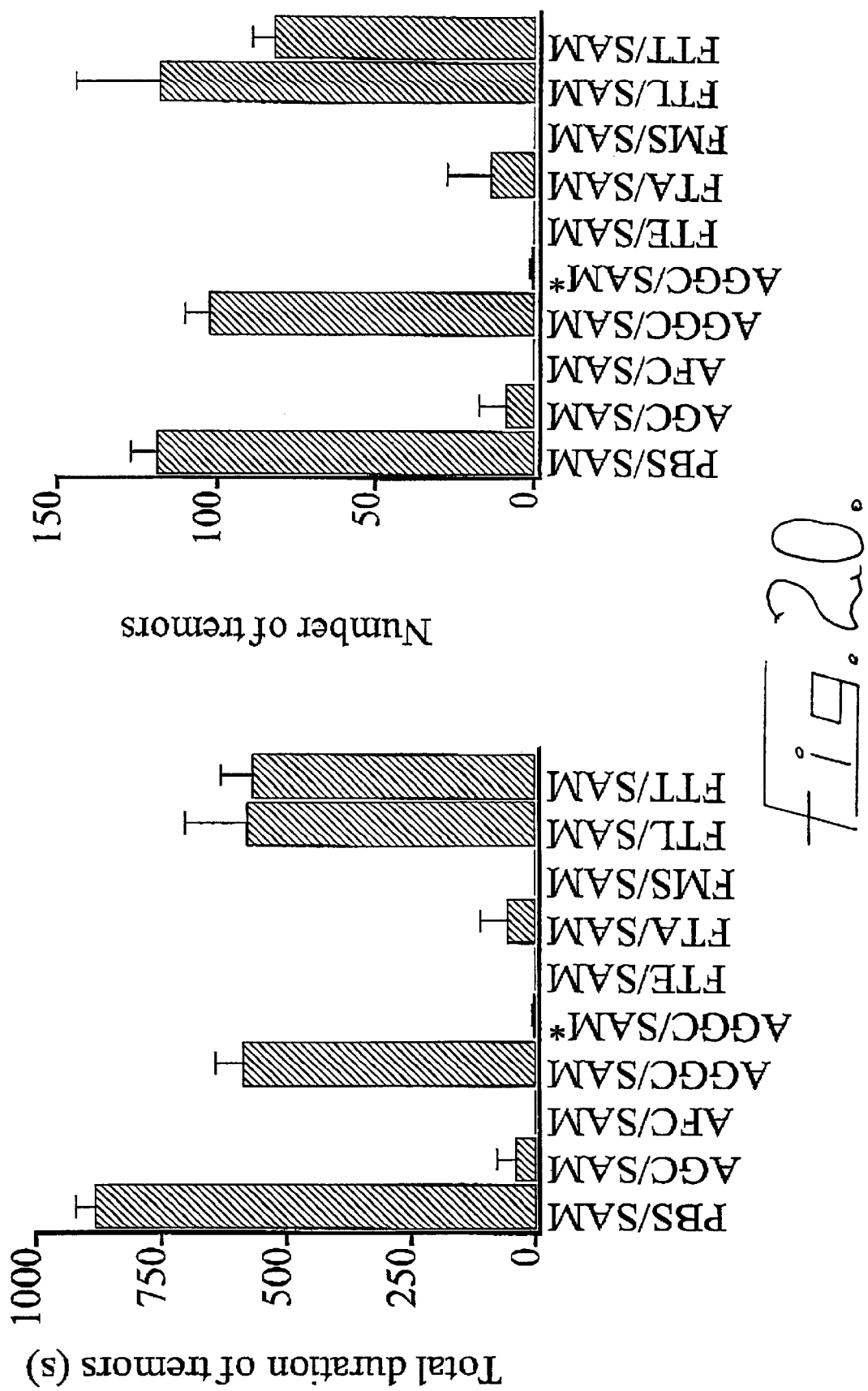
FIG. 20: Effect of Prenylcysteine Analogs on SAM-induced tremors. Cannulated rats were Icv injected with 1 µmol of N-acetylgeranylcysteine (AGC), N-acetylfarnesylcysteine (AFC), N-acetylgeranylgeranylcysteine (AGGC), farnesyl-2-mercaptoethanesulfonic acid (FTE), farnesylthioacetic acid (FTA), fanesylmercaptosuccinic acid (FMS), farnesylthiolactic acid (FTL) or farnesylthiotriazole (FTT), each dissolved in 5 µl of PBS. This was followed 5 min. later by an injection of 1 µmol of SAM dissolved in PBS. The animals were then monitored for 20 min. for the number and duration of tremors. AGGC/SAM* indicates a reinjection with 1 µmol SAM for animals that had been treated 2 days earlier with 1 µmol of AGGC and 1 µmol SAM.
Figure 21:
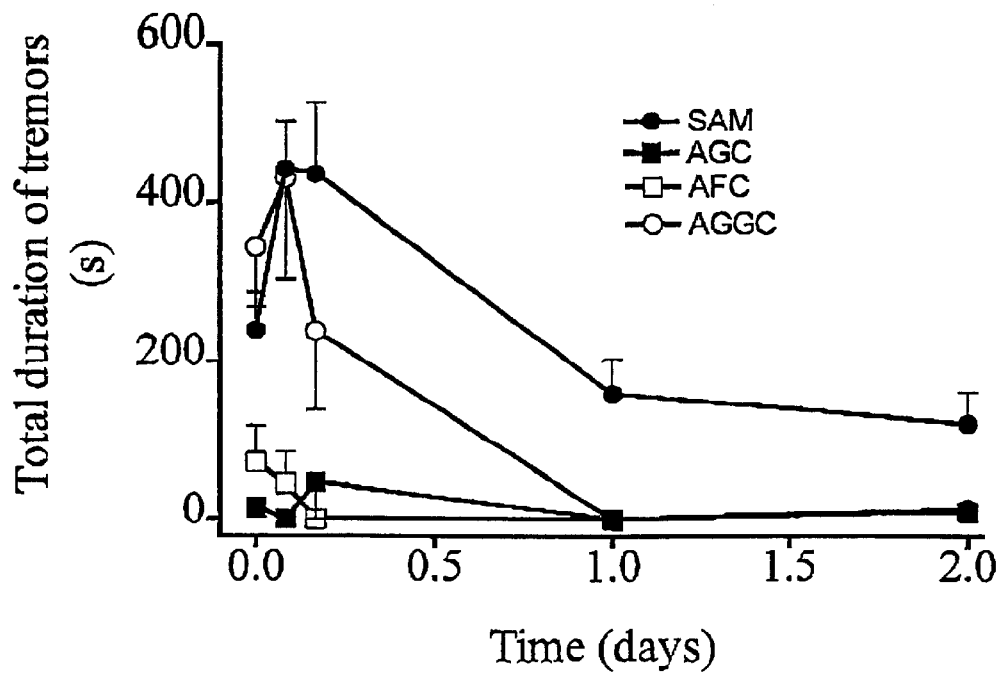
FIG. 21: Effect of Prenylcysteine analogs on repeated SAM injections. Cannulated rats were injected with 1 µmol of AGC, AFC, or AGGC, followed by repeated injections of 1 µmol SAM at 5 min., 2, 4, 24, and 48 hours later. Following each SAM injection, the total duration and number of tremors in each animal were monitored for 20 min. with a Tremor Monitor.
Figure 21:
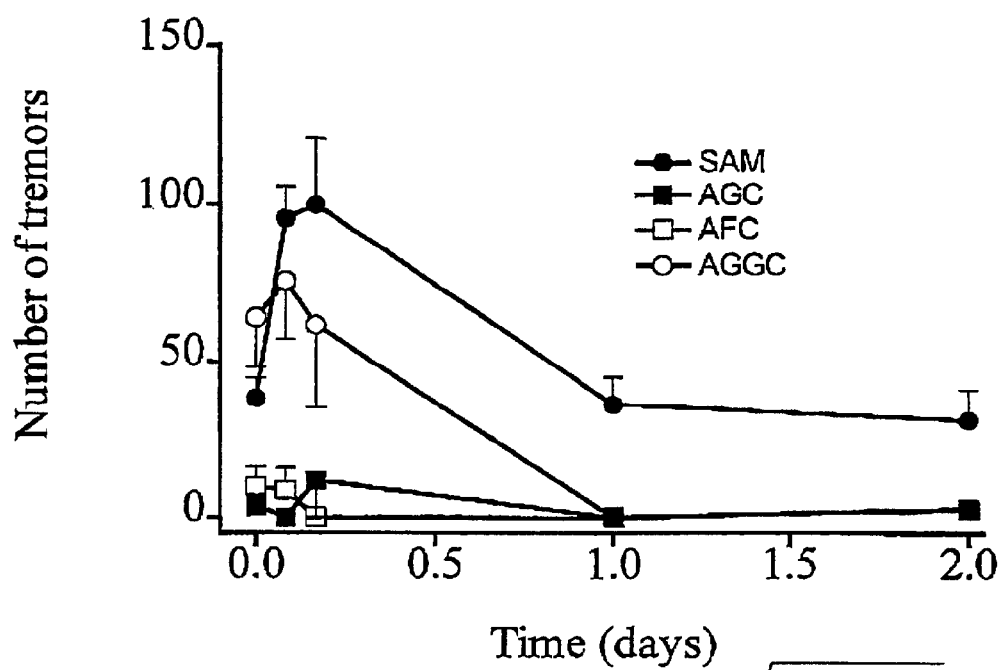

As shown in FIGS. 20 and 21, prenylcysteine analogs synthesized with either C10 geranyl, C15 farnesyl, and C20 geranylgeranyl compounds, were effective at preventing SAM-induced Parkinson's disease-like symptoms, although with varying pharmacokinetics. Their effectiveness was still significant 48 hours following administration.

Farnesylcysteine Analogs Induce Hyperactivity in Rats

Figure 18:
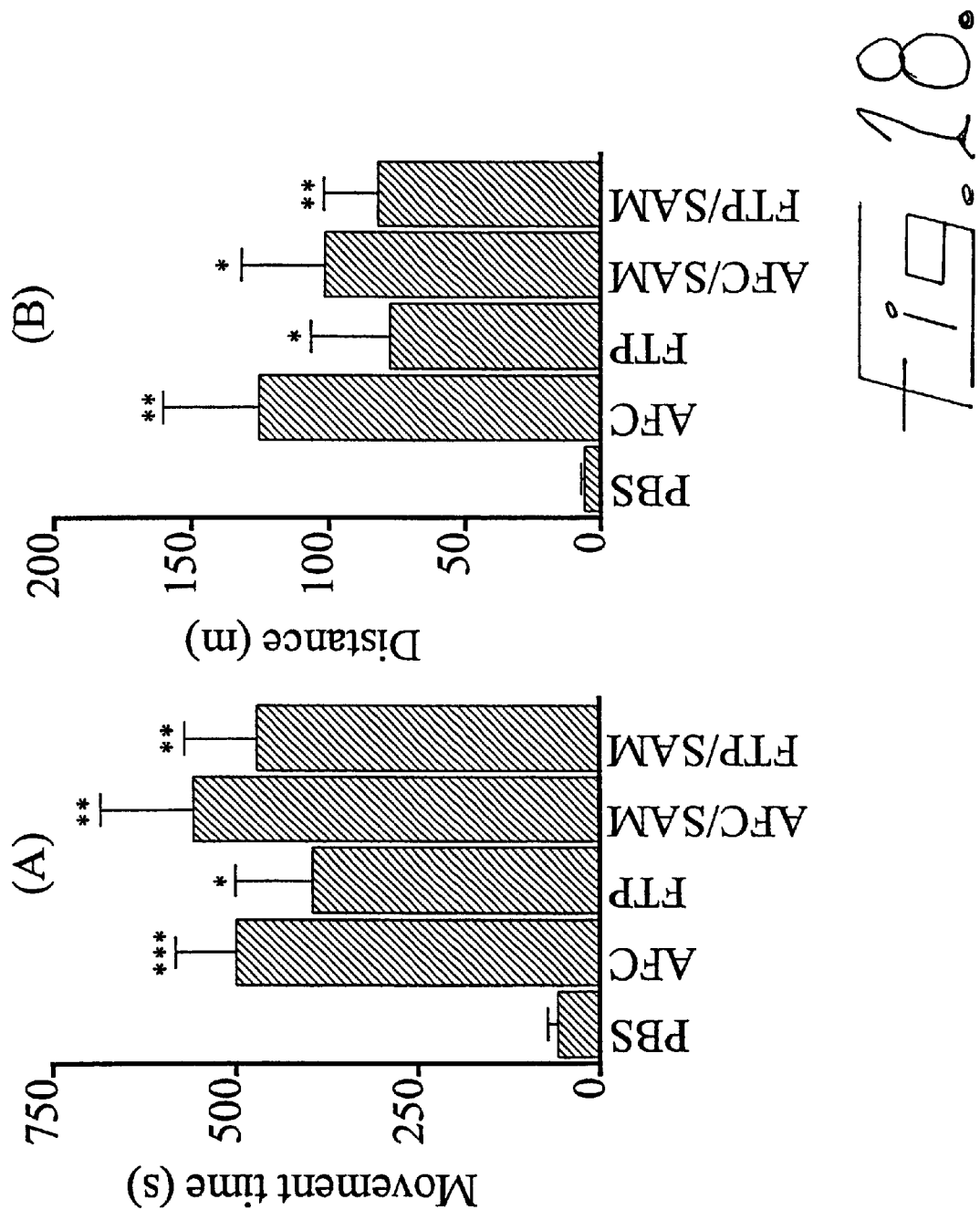
FIGS. 18(A and B): FC analogs increase the mobility of PBS- and SAM-treated animals. Cannulated rats were injected icv either with PBS alone, PBS and 1 mmol of AFC or FTP, 1 mmol of AFC or FTP followed 5 min later by 1 mmol of SAM. The mobility of each animal as indicated by the movement time (panel A) and the distance covered (panel B) was monitored over a period of 20 min in an Animal Activity Monitor. *$P<0.05$, $P<0.01$, *$P<0.001$ by unpaired t-test. The results are the means±S.E.M., N=6.

One characteristic feature of PD is hypokinesia which is marked by a decreased ability to initiate and continue movement. Our studies revealed that this was also a routine feature of SAM-treated rats. However, it was never observed in rats that received 1 mmmol of FC analog prior to treatment with SAM. On the contrary, a significantly higher degree of movement activity was observed in rats injected with either AFC or FTP alone or in combination with 1 mmmol of SAM. When these movements were measured in an Animal Activity Monitor for a period of 20 min, it was found that rats that received FC analogs with or without SAM spent between 400 and 560 seconds moving around the cage covering distances between 78 and 125 m. These values were significantly higher than those registered for the control animals that spent only about 60 sec in motion covering a distance of only about 6 m (FIG. 18).

Figure 19:
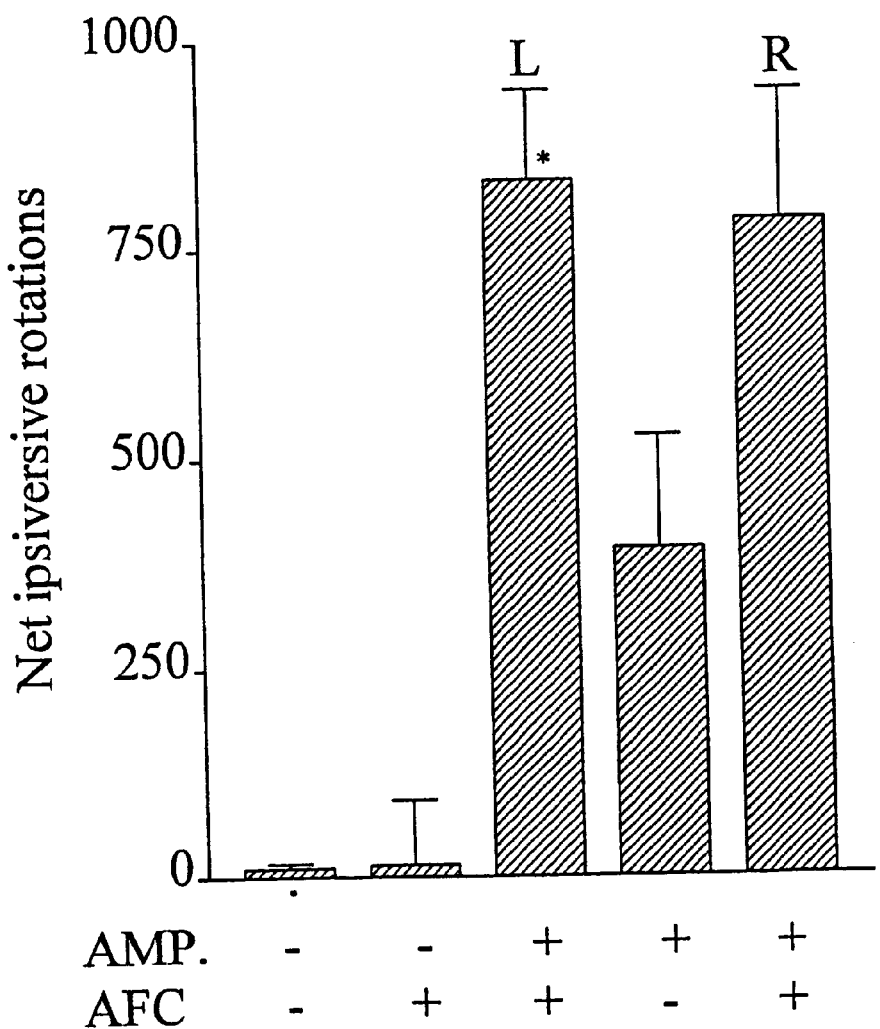
FIG. 19: FC analogs enhance the amphetamine-induced ipsiversive rotation of 6-hydroxydopamine-lesioned rats: Rats were lesioned by an acute injection of 6-OHDA into the left striatum as described in the methods. They were then cannulated for subsequent injections into either the left (L) or the right (R) lateral ventricles of the brain following the same coordinates as described in the methods. A week later, intra-peritoneal injections of either PBS or amphetamine (AMP) followed immediately by an icv injection of 1 mmol AFC were made. The net ipsiversive rotations (360° to the lesion side) were determined in a RotoScan Rotometer System. Two other independent experiments revealed similar results. *$P<0.05$ by unpaired t-test. The results are the means±S.E.M., N=6.

Farnesylcysteine analogs potentiate amphetamine-induced ipsiversive rotation of 6-hydroxydopamine-lesioned rats. An intrastriatal injection of 6-OHDA causes the destruction of dopaminergic neurons in the striatum resulting in a reduction of dopamine synthesis in the lesioned side. Differential release of dopamine between the intact and lesioned sides follows intraperitoneal (ip) administration of amphetamine resulting in rotational behavior of the animal towards the side of the lesion. Such ipsiversive rotation was observed when rats were injected with amphetamine 7 days after intrastriatal infusion with 6-OHDA. Rats injected ip with amphetamine displayed 390±130 ipsiversive rotations within 90 min. The rotation was increased 2-fold to 790±160 and 830±110 when rats received amphetamine and injections of AFC (1 mmmol in 5 mml of PBS) into either the right or left lateral ventricle, respectively. PBS or AFC alone induced only few net rotations (FIG. 19).

Statistical Analysis of the data was conducted using the GraphPad software program (GraphPad Software, Inc., San Diego Calif.). A P value, obtained by unpaired t-test, of less 0.05 was considered to be significant.

Discussion

Injection of SAM into the lateral cerebral ventricle of the experimental animals routinely induced symptoms characteristic of human Parkinsonism. Tremors, hypokinesia, rigidity and abnormal posture are the accepted behavioral features of PD. The narrow range between a relatively harmless dose and that which caused severe PD symptoms indicates the narrow safety margin of SAM. SAH, NADA and L-DOPA had little or no effect on the PD-like symptoms. SAH is a universal inhibitor of all SAM-dependent methylation reactions. Its lack of effect may be related either to its potency or inability to reach effective targets. It was believed initially that NADA, being a catecholamine like DA, would competitively inhibit SAM-dependent methylation of DA by COMT. Since this was found not to be the case, in addition to the fact that L-DOPA did not block the symptoms, it is possible that DA depletion may not have played a major role in precipitating the symptoms. L-DOPA, though not a cure, is often used to remedy the symptoms of PD. These data suggest that PD may be caused by an indirect abnormality in the DA signaling system whose less severe effects can be corrected by DA replenishment. It is worth noting that L-DOPA therapy gradually becomes less effective as PD progresses (Pfeiffer and Ebadi, 1994). The dose of SAM used in the present studies may be inducing symptoms comparable to the L-DOPA-insensitive later stages of the disease (Pfeiffer and Ebadi, 1994).

In studies involving PD patients, it has been reported that N-methylation of nicotinamide was 90 and 10 times higher than in controls and amyotrophic lateral sclerosis patients, respectively (Oertel et al., 1996). A 44% decrease in SAM levels, a 30% increase in the catalytic activity of L-methionine S-adenosyltransferase and a 50% decrease in the methylation capacity was detected in PD patients as compared to controls (Cheng et al., 1997). These reported results are in accordance with our findings in the present study and all demonstrate a difference in SAM metabolism between PD and non-PD patients that further underscores the role of SAM in Parkinsonism.

The onset of PD symptoms soon after injection of SAM led to an initial thought that SAM could be binding to a receptor system to cause its effects. For this reason, membranes were prepared to test this hypothesis. Membrane association of SAM-derived radioactivity that was inhibited by non-radioactive SAM and SAH but not $MPP^+$ was detected. This indicates that the association was indeed specific. The lack of reversibility after the association meant that classical binding was not responsible. Instead, the association could be due to a covalent transfer of the $^3$H-methyl group from [$^3$H-methyl]SAM to the membranes in a methylation process. Membrane-bound molecules capable of being methylated include lipids and proteins.

In order to understand whether the SAM-induced symptoms were due to methylation, cannulated rats were injected with [$^3$H-methyl]SAM under identical conditions as to induce the PD symptoms. The chromatographic mobility of the brain extracts from these animals on the gel-filtration column indicates that the methylated molecules involved are of sufficiently high molecular weight to elute within the 1 and 100 kDa fractionation range of the column. The fact that some of the methylated compounds eluted beyond the total volume, which is the point at which all molecules should have eluted, indicates possible interaction between the molecules and the solid medium. The bbgg complex of trimeric G-proteins was shown to interact with a gel-filtration column in this manner (Fukada et al, 1994). Since this interaction with the column packing was reversed by treatment with guanidine HCl, it is possible that the interaction between the methylated products and the chromatographic medium might have been mediated by another molecule in a complex. The effect on the elution of the methylated molecules by 6 M guanidine HCl could also indicate that sufficiently large molecules with complex three-dimensional structures may be involved. Intricate intra- and/or intermolecular interactions would have been disrupted by treatment with guanidine HCl. The resulting alterations in size and/or shape of the molecules would have altered the elution volumes of the methylated compounds as observed.

Methylation at isoprenylated C-terminals of isoprenylated proteins is a reversible secondary modification step (Perez-Sala et al., 1991) that may entail a point of homeostatic control. It is therefore possible that the reversal of PD-like symptoms in injected rats may be linked to demethylation. Indeed the symptoms reported here lasted only for about 90 min, given that they were induced in otherwise normal animals with functional mechanisms to counteract the effects of a temporary excess of SAM. They nevertheless raise the interesting questions as to what may be the case in individuals with an upregulated SAM synthesis and/or downregulated apparatus for counteracting the effects of excessive methylation.

Proteins that are prenylated at their carboxyl terminals are capable of accepting methyl groups and play significant roles in signaling pathways. Transmission by dopamine, the neurotransmitter involved in PD, is mediated by the dopamine receptor which interacts with trimeric G-proteins (Gudermann et al, 1996). The γ-subunit of this complex is isoprenylated, exists in a dimeric complex with the bb-subunit and is capable of undergoing reversible carboxyl methylation (Perez-Sala et al, 1991). The prenylation also accounts for the activation or inhibition of various adenylyl cyclases (Iniguez-Lluhi et al., 1992) thus indicating that the modified C-terminal end may contain significant functional information.

Based on this knowledge, and the fact that a molecule of about 5 kDa that possibly exists in a complex was carboxymethylated following in vivo treatment with SAM, we sought to understand whether FC analogs would have any effect on the SAM induced PD-like symptoms. FC analogs have been shown to influence various other cellular phenomena including protein methylation (Perez-Sala et al, 1992), ion transport (Xu et al, 1996) and superoxide production (Ding et al, 1994). If, however, methylation of prenylated proteins were involved in PD-like symptoms, FC analogs might inhibit the process and reverse the SAM-induced effects. According to our prediction, FC analogs substantially reversed the PD-like symptoms, suggesting that excessive methylation of prenylated proteins alters the pattern of isoprene-mediated protein-protein interactions precipitating the observed PD-like symptoms. The observation that FC analogs reverse the hypokinesia to the point of inducing hyperactivity indicates that normal behavioral movements probably require a carefully regulated balance between methylated and unmethylated isoprenylated protein moieties.

Amphetamine induces the release of and inhibits re-uptake of dopamine by dopaminergic neurons. When D-amphetamine is administered to an animal whose striatum has been lesioned on one side, the animal exhibits unidirectional rotational movement (ipsiversive) to the lesioned side (Labandeira-Garcia et al., 1996, Moser et al., 1996). This is due to the fact that more DA is synthesized by the intact side and is thus released following stimulation with amphetamine. The potentiation of amphetamine-induced rotation of 6-OHDA-lesioned rats and the lack of significant net rotational behavior attributable to AFC alone points to the fact that AFC could be influencing a process triggered by the binding of the released dopamine to the receptor. Released dopamine binds to its post-synaptic receptors inducing a chain of intracellular events that involve the trimeric G-proteins, of which the γ-subunit is prenylated. Although it is unclear at this point where AFC may be exerting the observed physiological effects, the fact that AFC had a significant effect only after amphetamine-induced dopamine release suggests that it could be affecting a process downstream to the dopamine receptor such as at the level of the intracellular second messenger/effector sites where the G-protein βγ-complex interacts with effector enzymes and ion channels (Clapham and Neer, 1997). These results are in agreement with previously published work showing that FC analogs and compounds that influence the methylation of isoprenylated proteins also affect physiological processes triggered through G-protein anchored receptor systems (Regazzi et al, 1995, Scheer and Gierschik, 1993, 1995, Regazzi et al, 1995, Capdevila et al, 1997).

The G-protein γ-subunits in the brain are modified by all trans-geranylgeranyl moieties which are C20 isoprene groups. Enzyme studies on the methylation of prenylcysteine analogs reveal about a 4-fold higher affinity by the prenylated protein methyltransferase (PPMTase) for the C20 geranylgeraylated over the C15 farnesylated substrates (Volker et al, 1991). If the effects of the FC analogs employed in this study are due to interference with the brain G-protein system, this may imply that the doses used could be significantly reduced if the C20 prenyl analogs were used in order to exploit their higher affinity for the effector sites. The C20 analogs were found to be more effective at inducing insulin release by permeabilized HIT-T15 cells than the C15 analogs while the C10 derivatives were ineffective (Regazzi et al, 1995).

In summary, this study demonstrates that the injection of SAM into the lateral ventricle of rats induces quantifiable tremors and the other motor deficits evident in PD. Use of [$^3$H-methyl]SAM revealed the methylation of molecules of about 5 kDa that possibly exist in a complex and released radioactive methyl groups on incubation in a basic medium, suggesting the presence of carboxyl methyl esters. The PD-like symptoms were blocked by FC analogs modeled on the C-terminal prenylated portion of the Gγ-subunit of trimeric G-proteins that are involved in the signaling by such molecules as dopamine, a neurotransmitter whose depletion is generally implicated in the symptoms of PD. The FC analogs reversed the hypokinesia in the experimental animals and also significantly increased their activity over SAM-only and PBS-only treated animals. The behavioral effects induced by SAM and those caused by the overwhelming presence of injected FC analogs suggest the importance of a careful balance between the methylated and unmethylated moieties in maintaining normal neural function. The potentiation of ipsiversive turning in 6-OHDA-lesioned rats by AFC only in the presence of amphetamine indicates that FC and its analogs are influencing events preceded by the release of dopamine into the synapse. These data indicate that FC and FC analogs substantially reverse PD-like symptoms resulting from a methylation/demethylation imbalance in the neural tissues.

Accordingly, there have been disclosed a typical preferred embodiment of the invention, and although specific terms are employed, the terms are used in a descriptive sense only and not for purposes of limitation. The invention has been described in considerable detail with specific reference to the given experimental examples. It will be apparent, however, that various modifications and changes can be made within the spirit and scope of the invention as described in the foregoing specification and as defined in the appended claims.

That which is claimed:

1. A method of substantially reversing a methylation/demethylation imbalance in mammalian neural tissue thereby improving neuromodulator function, the method comprising contacting the neural tissue with an effective amount of a compound comprising a prenylcysteine or a pharmaceutically acceptable analog thereof.

2. The method of claim 1, wherein the prenylcysteine comprises farnesylcysteine.

3. The method of claim 1, wherein the prenylcysteine comprises geranylcysteine.

4. The method of claim 1, wherein the prenylcysteine comprises N-acetylfarnesylcysteine.

5. The method of claim 1, wherein the prenylcysteine comprises geranylgeranylcysteine.

6. The method of claim 1, wherein the pharmaceutically acceptable analog comprises farnesyl-2-mercaptoethanesulfonic acid.

7. The method of claim 1, wherein the pharmaceutically acceptable analog comprises farnesylthioacetic acid.

8. The method of claim 1, wherein the pharmaceutically acceptable analog comprises farnesylmercaptosuccinic acid.

9. The method of claim 1, wherein the pharmaceutically acceptable analog comprises farnesylthiolactic acid.

10. The method of claim 1, wherein the pharmaceutically acceptable analog comprises farnesylthiotriazole.

11. The method of claim 1, wherein the compound comprises a prenylcysteine or analog thereof selected from farnesylcysteine, N-acetylgeranylcysteine, N-acetylfanesylcysteine, N-acetylgeranylgeranylcysteine, farnesyl-2-mercaptoethanesulfonic acid, farnesylthioacetic acid, and farnesylmercaptosuccinic acid.

12. The method of claim 1, wherein the neuromodulator comprises a neurotransmitter receptor site.

13. The method of claim 1, wherein the neuromodulator comprises a dopamine receptor site.

14. A method for treatment of a mammalian neurological disease characterized by impaired neuromodulator function, the method comprising administering a therapeutically effective amount of a composition including a compound of a prenylcysteine or an analog thereof in a pharmaceutically acceptable carrier.

15. The method of claim 14, wherein the impairment of neuromodulator function is characterized by a methylation/demethylation imbalance in neural tissue.

16. The method of claim 14, wherein the composition comprises at least one compound selected from farnesylcysteine, N-acetylgeranylcysteine, N-acetylfanesylcysteine, N-acetylgeranylgeranylcysteine, farnesyl-2-mercaptoethanesulfonic acid, farnesylthioacetic acid, and farnesylmercaptosuccinic acid.

17. The method of claim 14, wherein the composition further comprises a therapeutically effective amount of L-DOPA.

18. The method of claim 14, wherein the neuromodulator comprises a neurotransmitter receptor site.

* * * * *

UNITED STATES PATENT AND TRADEMARK OFFICE
CERTIFICATE OF CORRECTION

PATENT NO. : 6,372,793 B1
APPLICATION NO. : 09/642576
DATED : April 16, 2002
INVENTOR(S) : Nazarius S. Lamango and Clivel G. Charlton Page 1 of 1

It is certified that error appears in the above-identified patent and that said Letters Patent is hereby corrected as shown below:

In the Specification

Column 1, line 12, please amend as follows:

This invention was made with government support under grants GM 08111 35 and G12 RR 03020 which was awarded by the National institutes of Health. The government has certain rights in the invention.

Signed and Sealed this
Twenty-seventh Day of October, 2015

Michelle K. Lee
*Director of the United States Patent and Trademark Office*